US012702582B2

(12) United States Patent
Baratier et al.

(10) Patent No.: US 12,702,582 B2
(45) Date of Patent: Aug. 11, 2026

(54) MANDIBULAR REPOSITIONING DEVICE

(71) Applicant: ResMed SAS, Saint Priest (FR)

(72) Inventors: Ludovic Baratier, Cailloux-sur-Fontaines (FR); Yann Palomino, Saint-Priest (FR)

(73) Assignee: RESMED SAS, Saint Priest Cedex (FR)

( * ) Notice: Subject to any disclaimer, the term of this patent is extended or adjusted under 35 U.S.C. 154(b) by 0 days.

(21) Appl. No.: 18/150,550

(22) Filed: Jan. 5, 2023

(65) Prior Publication Data

US 2023/0149205 A1 May 18, 2023

Related U.S. Application Data

(60) Continuation of application No. 16/509,534, filed on Jul. 12, 2019, now Pat. No. 11,576,809, which is a (Continued)

(30) Foreign Application Priority Data

May 3, 2013 (EP) .................................... 13305585

(51) Int. Cl.
*A61F 5/56* (2006.01)
*A61C 7/08* (2006.01)

(Continued)

(52) U.S. Cl.
CPC ................ *A61F 5/566* (2013.01); *A61C 7/08* (2013.01); *A61C 7/36* (2013.01);

(Continued)

(58) Field of Classification Search
CPC ...... A61F 5/56; A61F 5/566; A61F 2005/563; A61F 5/58; A61F 5/0006; A61C 7/08;

(Continued)

(56) References Cited

U.S. PATENT DOCUMENTS 2,707,951 A * 5/1955 Shackelford ......... A63B 71/085
128/861
3,107,668 A 10/1963 Thompson (Continued)

FOREIGN PATENT DOCUMENTS

EP 2 575 706 A1 4/2013
FR 2 816 203 5/2002

(Continued)

OTHER PUBLICATIONS

Partial European Search Report issued in corresponding European Application No. 14167067.9 dated Jul. 25, 2014.

(Continued)

*Primary Examiner* — Victoria Hicks Fisher
(74) *Attorney, Agent, or Firm* — Nixon & Vanderhye P.C.

(57) ABSTRACT

An intra-oral device includes an upper splint, a lower splint and a pair of lateral connecting rods. Each connecting rod has a first rod end that connects to the lower splint and a second rod end that connects to the upper splint. The connecting rods are configured to maintain the mandible in an advanced position relative to the maxilla. The upper splint includes at least one upper gutter portion that retains the upper splint on the maxilla. The lower splint includes at least one lower gutter portion that retains the lower splint on the mandible. The thickness of the at least one upper gutter portion and/or the at least one lower gutter portion may vary across the profile of the teeth.

27 Claims, 27 Drawing Sheets

Related U.S. Application Data division of application No. 14/269,395, filed on May 5, 2014, now Pat. No. 10,363,160, which is a continuation-in-part of application No. 14/268,345, filed on May 2, 2014, now abandoned.

(51) Int. Cl.

| | |
|---|---|
| ***A61C 7/36*** | (2006.01) |
| *A61B 17/00* | (2006.01) |
| *A61B 34/10* | (2016.01) |

(52) U.S. Cl.

CPC ............... *A61B 2017/00526* (2013.01); *A61B 2034/108* (2016.02); *A61F 2005/563* (2013.01); *G05B 2219/45167* (2013.01)

(58) Field of Classification Search

CPC ....... A61C 7/36; A61C 19/063; A61C 19/066; A63B 71/085; A63B 2071/086; A63B 2071/088

See application file for complete search history.

(56) References Cited

U.S. PATENT DOCUMENTS

| | | | | |
|---|---|---|---|---|
| 3,314,423 | A | 4/1967 | Boatwright et al. | |
| 3,407,808 | A | 10/1968 | Baldwin | |
| 4,419,992 | A | 12/1983 | Chorbajian | |
| 4,944,310 | A | 7/1990 | Sullivan | |
| 5,003,994 | A | 4/1991 | Cook | |
| 5,267,862 | A | 12/1993 | Parker | |
| 5,338,190 | A | 8/1994 | Tregillis | |
| 5,692,521 | A | 12/1997 | Leaure-Nelson | |
| 5,876,199 | A | 3/1999 | Bergersen | |
| 6,302,686 | B1 | 10/2001 | Chott | |
| 10,363,160 | B2 * | 7/2019 | Baratier | A61F 5/566 |
| 2003/0224314 | A1 | 12/2003 | Bergersen | |
| 2005/0016547 | A1 | 1/2005 | Mousselon et al. | |
| 2005/0150504 | A1 | 7/2005 | Heeke et al. | |
| 2008/0236597 | A1 | 10/2008 | Bergersen | |
| 2009/0159089 | A1 * | 6/2009 | Jansheski | A61F 5/566 128/861 |
| 2010/0261133 | A1 | 10/2010 | Lax | |
| 2012/0028205 | A1 | 2/2012 | Metz | |
| 2013/0140289 | A1 | 6/2013 | Baratier | |
| 2014/0326253 | A1 | 11/2014 | Baratier et al. | |
| 2015/0250642 | A1 * | 9/2015 | Miquel | A61C 7/36 128/848 |
| 2019/0336322 | A1 | 11/2019 | Baratier et al. | |

FOREIGN PATENT DOCUMENTS

| | | |
|---|---|---|
| FR | 2 935 261 | 3/2010 |
| WO | 2011/147985 A1 | 12/2011 |

OTHER PUBLICATIONS

Extended European Search Report issued in corresponding European Application No. 14167067 dated Oct. 16, 2014.

Extended European Search Report mailed Feb. 8, 2017 in European Application No. 16172453.9 (8 pages).

Canadian Office Action mailed Feb. 6, 2017 in Canadian Application No. 2,850,946 (6 pages).

Dictionary.com, "calculate", https://www.dictionary.com/browse/calculate.

Office Action dated Apr. 28, 2021 issued in European Application No. 16172453.9 (2 pages).

* cited by examiner

MANDIBULAR REPOSITIONING DEVICE

CROSS REFERENCE TO RELATED APPLICATIONS

This application is a continuation of U.S. application Ser. No. 16/509,534, filed Jul. 12, 2019, which is a divisional of U.S. application Ser. No. 14/269,395, filed May 5, 2014, which is a continuation-in-part of U.S. application Ser. No. 14/268,345, filed May 2, 2014, which claims priority to EP Application No. 13 30 5585.5, filed May 3, 2013, the entire contents of each of which are hereby incorporated by reference.

BACKGROUND OF THE INVENTION

1.1 (1) Field of the Invention

The present technology relates to an intraoral orthosis device for preventing and/or treating snoring and/or obstructive sleep apnea. In particular, the present technology relates to a mandibular repositioning device (MRD) or Mandibular advancement device (MAD) for treating and/or preventing snoring and/or obstructive sleep apnea.

1.2 (2) Description of the Related Art

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. (West, “Respiratory physiology—the essentials”).

Chronic snoring is a condition affecting a considerable proportion of the population, estimated at 40% by some studies. During sleep, the patient’s throat muscles relax, causing a narrowing of the pharynx. The consequence of this narrowing is an increase in the speed of the inhaled air caused by a venturi-type effect. The air excites the flexible part of the soft palate and uvula and these begin to vibrate noisily. The noise created in this way can reach up to 90 decibels.

Obstructive Sleep Apnea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods of at least 10 seconds duration, typically of 30 to 120 seconds duration, sometimes 200 to 300 times per night. The patient often resumes breathing in a sudden and noisy manner. It often causes excessive daytime somnolence, and it may cause cardiovascular disease and brain damage. The syndrome is a common disorder, particularly in middle aged overweight males, although a person affected may have no awareness of the problem.

(U.S. Pat. No. 4,944,310 (to Sullivan).)

Therapy

Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

1.2.1 PAP Device

The air at positive pressure is typically supplied to the airway of a patient by a PAP device such as a motor-driven blower. The outlet of the blower is connected via a flexible delivery conduit to a patient interface that delivers the pressurized air to the airways of the patient. However, some patients do not tolerate CPAP therapy well and so alternative therapies are available.

1.2.2 Mandibular Repositioning

A mandibular repositioning device (MRD) or mandibular advancement device (MAD) is one of the treatment options for sleep apnea and snoring. It is an adjustable intra-oral appliance, available from a dentist or other supplier, which holds the lower jaw (mandible) in a forward position during sleep. The MAD is a removable device that a patient inserts into their mouth, prior to going to sleep, and removes, following sleep. Thus, the MAD is not designed to be worn all of the time. The MAD may be custom made, or produced in a standard form and include a bite impression portion designed to allow fitting to a patient’s teeth. The mechanical protrusion of the lower jaw expands the space behind the tongue, puts tension on the pharyngeal walls to reduce collapse of the airway and diminish palate vibration.

A mandibular advancement device comprises an upper splint that is intended to engage with or fit over teeth on the upper jaw (or maxilla) and a lower splint that is intended to engage with or fit over teeth on the upper jaw (or mandible). The upper and lower splints are connected together laterally via a pair of connecting rods. The pair of connecting rods is preferably fixed symmetrically on both sides of the jaw. Each rod is attached to the upper splint and the lower splint. Whilst each rod is generally attached to the upper splint and the lower splint at its respective ends, this does not have to be the case and the attachment may be effected by other portions of the rod.

The length of the connecting rods is selected such that when the MAD is placed in a user’s mouth the mandible is held in an advanced position. The length of the connecting rods may be adjusted to change the level of protrusion of the mandible. A dentist may determine a preferred level of protrusion for the mandible that will determine the length of the connecting rods.

Some MADs are structured to push the mandible forward relative to the maxilla while other MADs, such as the ResMed Narval CC™ MAD, are designed to retain the mandible in a forward position. This device also reduces or minimises dental and temporo-mandibular joint (TMJ) side effects. Thus, it is configured to prevent or at least minimise any movement of one or more of the teeth caused by the applied pressure. For instance, document US2005016547 discloses a MAD with an upper groove and a lower groove designed to line respectively with the upper jaw and the lower jaw. The grooves are linked together by two tie rods of such length that the lower jaw is maintained in an extended position relative to the upper jaw.

1.2.3 Bruxism Treatment

Bruxism is the excessive grinding of the teeth and/or excessive clenching of the jaw. Some treatment devices known as occlusal splints cover the teeth of the upper and/or lower jaw to mechanically protect them. There are available intra-oral devices including partial or full-coverage splints, i.e. splints fitting over some or all of the teeth. They are typically made of plastic (e.g. acrylic) and can be hard or soft. A lower appliance can be worn alone, or in combination with an upper appliance.

BRIEF SUMMARY OF THE TECHNOLOGY

The present technology is directed towards a mandibular repositioning device used in the amelioration, treatment, or prevention of snoring or obstructive sleep apnea having either one or more of improved comfort, cost, efficacy, retention, ease of use and manufacturability, or at least providing a useful alternative to existing devices.

A first aspect of the present technology relates to an apparatus used in the amelioration, treatment or prevention of snoring and/or obstructive sleep apnea by repositioning the lower jaw of a user in a forward position.

One form of the present technology comprises a mandibular advancement device or intra-oral device that is configured for comfortable use by the user.

Another aspect of one form of the present technology is a mandibular advancement device having thickness of at least one gutter portion which varies across the profile of the teeth. This is to say that the cross-section of the gutter portion may have variable thickness. Preferably a retention portion and its profile are structured to match the profile of the teeth.

Another aspect of one form of the present technology is a method of designing a mandibular advancement device (MAD) using a computer aided design process, wherein the MAD is designed to include a retention profile calculated based on the area of a patient's teeth available for gripping.

Another aspect of one form of the present technology is a mandibular advancement device having a gutter portion designed to grip over a plurality of teeth to retain the device on the jaw.

One form of the present technology comprises a mandibular advancement device that provides a strong grip, reduced pressure on the teeth and/or a substantial elasticity.

Another aspect of one form of the present technology is the curved lower end of gutter edges on the splints, preferably improving comfort.

One form of the present technology comprises an angled band portion, which may be inclined relative to a plane perpendicular to the sliding plane and along the axis of insertion. The band portion may be angled to follow the angle of the incisors to reduce protrusion into the inside of the lips.

One form of the present technology comprises a slot angled to prevent or minimise unclipping of the connecting rods during cleaning. The angle of the slot may be designed relative to the axis of the connecting rod and may be adjustable.

Another aspect of one form of the present technology is an MAD including a connection point on a lower splint that is structured to support the mucosa of the cheek.

One form of the present technology comprises a connecting rod slot counter sunk within elevated connection point of the lower splint.

Another aspect of the present technology relates to using a version of the intra-oral described herein to treat Bruxism. The intra-oral device may include no or only minor adjustments for use to treat Bruxism.

One form of the present technology comprises an intra-oral device having upper and lower splints that cover all or most of the teeth and are coupled together via rods that are set at no or 0 protrusion to treat Bruxism. The lower splint may include wings or triangular portions from which the rods are attached.

In another form of the present technology is an intra-oral device comprising separate upper and lower splints that cover all or most of the teeth, wherein the splints are not coupled together (i.e. no rods are attached between the upper and lower splints).

In a further form of the present technology is an intra-oral device adapted to simultaneously protrude the lower jaw forward to treat sleep disordered breathing and to cover all or most of the teeth to treat or prevent Bruxism.

As referred to herein, a neutral position of the mandible relative to the maxilla is the natural closing position. In other words the mandible in not forced or repositioned to an advanced position and is not forced or repositioned by the device to an retracted position as generally seen in a direction parallel to the oclussal plane. A neutral position is a position with an advancement of about 0 mm. If the user does not suffer from a sleep disorder such as sleep apnea, a neutral position may be appropriate to avoid or reduce bruxism without the discomfort caused by advancing the mandibular. On the other hand, if both bruxism and sleep apneas are to be treated a device adapted to cause an advanced position of the mandibular may be suitable.

Of course, portions of the aspects may form sub-aspects of the present technology. Also, various ones of the sub-aspects and/or aspects may be combined in various manners and also constitute additional aspects or sub-aspects of the present technology. Alternatively or additionally, the disclosed technology could also be described by one or several of the following aspects. In particular, an aspect with a preferred back-reference to one or more other aspects may also be understood as an independent aspect.

1a. An intra-oral device, preferably designed to fit in a patient's mouth, comprising:

an upper splint (7100), preferably structured to engage with at least a portion of one or more teeth on the maxilla, wherein the upper splint (7100) includes at least one upper gutter portion (7110), that preferably engages with a portion of one or more teeth on the maxilla, to retain the upper splint on the maxilla; and/or a lower splint (7200), preferably structured to engage with at least a portion of one or more teeth on the mandible, wherein the lower splint (7200) include at least one lower gutter portion (7210), that preferably engages with a portion of one or more teeth on the mandible, to retain the lower splint on the mandible.

1b. The intra-oral device of aspect 1a, wherein the device is a mandibular device and/or a bruxim splint.

1c. The intra-oral device of aspect 1a or 1b, wherein the device comprises the upper splint (7100), the lower splint (7200), and a pair of lateral connecting rods (7300), each connecting rod having a first rod end (7310) that connects to the lower splint and a second rod end (7320) that connects to the upper splint, preferably such that, in use when the user's mouth is closed, the connecting rods are positioned parallel to the Frankfort plane.

1d. The intra-oral device of any one of aspects 1a to 1c, wherein the connecting rods (7300) are configured to maintain the mandible in a neutral position relative to the maxilla.

1e. The intra-oral device of any one of aspects 1a to 1d, wherein the connecting rods (7300) are configured to maintain the mandible in an advanced position relative to the maxilla.

1f. The intra-oral device of any one of aspects 1a to 1d, wherein the upper splint (7100) is adapted to cover all teeth of the respective upper jaw and/or the lower splint (7200) is adapted to cover all teeth of the respective lower jaw.

2a. An intra-oral mandibular advancement device, preferably designed to fit in a patient's mouth, comprising:

an upper splint (7100), preferably structured to engage with at least a portion of one or more teeth on the maxilla;

a lower splint (7200), preferably structured to engage with at least a portion of one or more teeth on the mandible; and a pair of lateral connecting rods (7300), each connecting rod having a first rod end (7310) that connects to the lower splint and a second rod end (7320) that connects to the upper splint, preferably such that, in use when the user's mouth is closed, the connecting rods are positioned parallel to the Frankfort plane, wherein the connecting rods are configured to maintain the mandible in an advanced position relative to the maxilla, wherein the upper splint includes at least one upper gutter portion (7110), that preferably engages with a portion of one or more teeth on the maxilla, to retain the upper splint on the maxilla, wherein the lower splint include at least one lower gutter portion (7210), that preferably engages with a portion of one or more teeth on the mandible, to retain the lower splint on the mandible.

2b. The intra-oral mandibular device according to aspect 1, wherein the thickness of the at least one upper gutter portion and/or the at least one lower gutter portion varies across the profile of at least a portion of one or more teeth.

2c. The intra-oral device according to any one of aspects 1a to 1f or 2a, wherein a retention portion of at least one of the at least one upper gutter portion and the at least one lower gutter portion has a varied thickness profile.

3. The intra-oral device according to any one of aspects 1a to 1f or to 2a, 2b or 2c, wherein the at least one upper gutter portion is profiled to match the contours of the at least a portion of one or more teeth on the maxilla to improve retention of the upper splint.

4. The intra-oral device according to any one of the preceding aspects, wherein the at least one lower gutter portion is profiled to match the contours of the at least a portion of the one or more teeth on the mandible to improve retention of the lower splint.

5. The intra-oral device according to any one of aspects 2 to 4, wherein the retention portion is structured to match the profile of the at least a portion of the one or more teeth on the maxilla or mandible.

6. The intra-oral device according to any one of the preceding aspects, wherein the retention portion extends along the crown region of the at least a portion of the one or more teeth engaged by the gutter portion.

7. The intra-oral device according to aspect 6, wherein the retention portion is located at a side portion of the crown region.

8. The intra-oral device according to any one of the preceding aspects, wherein the at least one upper gutter portion, which is preferably adapted to elastically clip on at least one tooth or at least a portion of one or more teeth located in the upper gutter portion, and/or the at least one lower gutter portion is adapted to elastically clip on at least one tooth or at least a portion of one or more teeth located in the lower gutter portion.

9. The intra-oral device according to any one of the preceding aspects, wherein the at least one upper gutter portion and/or the at least one lower gutter portion each comprise, at the inner side wall facing the at least one tooth or at least a portion of one or more teeth, at least one undercut portion (7266), the undercut portion (7266) being adapted to hold the device on the tooth or at least a portion of one or more teeth, at least to support at least one of the retention or clipping of the device.

10. The intra-oral device according to aspect 9, wherein the undercut portion extends substantially along the tooth's side wall (b) from an apex (a) of the tooth's side wall (b) in an inward direction towards the gingival part of the tooth.

11. The intra-oral device according to aspect 9 or 10, wherein the undercut portion defines an undercut (u), the undercut (u) preferably being adapted to interlock the respective upper splint and/or lower splint to the at least one tooth or at least a portion of one or more teeth on the maxilla or mandible respectively.

12. The intra-oral device according to any one of the preceding aspects, wherein the at least one upper gutter portion (7110) and/or the at least one lower gutter portion (7210) comprise(s) a sliding plane surface (7160, 7260).

12a. The intra-oral device of aspect 12, wherein the sliding plane surface (7160, 7260) of one of the upper and lower gutter portions (7110, 7210) is in contact with the other of the upper and lower gutter portions (7110, 7210).

12b The intra-oral device of aspect 12 or 12a, wherein the sliding plane surface (7160, 7260) is substantial flat and, in use, is substantially parallel to the occlusal plane.

12c The intra-oral device of aspect 12, 12a or 12b, wherein the sliding plane surface extends along a major part or the entire width of the tooth.

12d The intra-oral device of any one of aspects 12 to 12c, wherein the sliding plane surface extends along the tooth or at least a portion of one or more teeth in a cross sectional view of the gutter portion.

13. The intra-oral device according to aspect 12, wherein the sliding plane surface joins the side wall of the respective gutter portion (7110, 7210) in at least one first joining section (7264), and wherein the thickness (EPa) of the side wall of the respective gutter portion (7110, 7210) in the area of the apex (a) of the tooth or at least a portion of one or more teeth is reduced compared to the thickness (EPj) of the side wall in the first joining section.

14. The intra-oral device according to any one of the preceding aspects, wherein the undercut portion intersects with an inner receiving portion (7268) of the side wall of the respective gutter portion (7110, 7210) in a second joining section (7269).

15. The intra-oral device according aspect 14, wherein the thickness (EPa) of the side wall of the respective gutter portion (7110, 7210) in the area of the apex (a) of the tooth or at least a portion of one or more teeth is reduced compared to at least one of the thickness (EPl)

of the side wall in the second joining section and the thickness (EPm) of the side wall of the inner receiving portion.

16. The intra-oral device according aspect 14 or 15, wherein the inner receiving portion may angle outwardly and, in use, away from the gingival part.

17. The intra-oral device according to any one of the preceding aspects, wherein the lower splint includes a lower splint connection point (7230) for connection of the first rod end (7310).

18. The intra-oral device according to aspect 17, wherein the lower splint connection point is elevated in the application position relative to the major part of the lower splint and/or relative to the at least a portion of one or more lower teeth.

19. The intra-oral device according to any one of the preceding aspects, wherein the lower splint connection point (7230) includes a first slot (7232) and/or the first rod end (7310) includes a first rod pin (7312) configured to be received in the first slot.

20. The intra-oral device preferably according to aspect 19, wherein, in a closed configuration of the device, the longitudinal axis of the first slot and the longitudinal axis of the connecting rod are arranged in a first obtuse angle (α).

21. The intra-oral device according to any one of the preceding aspects, wherein the upper splint includes an upper splint connection point (7130) for connection of the second rod end (7320).

22. The intra-oral device according to aspect 21, wherein the upper splint connection point (7130) includes a second slot (7132) and/or the second rod end (7320) includes a second rod pin (7322) configured to be received in the second slot.

23. The intra-oral device preferably according to aspect 22, wherein, in a closed configuration of the device, the longitudinal axis of the second slot and the longitudinal axis of the connecting rod are arranged in a second obtuse angle (β).

24. The intra-oral device preferably according to any one of aspects 19 to 23, wherein the first slot is counter sunk on the lower splint connection point.

25. The intra-oral mandibular advancement device preferably according to any one of aspects 19 to 24 wherein the second slot is counter sunk on the upper splint connection point.

26. The intra-oral device preferably according to any one of the preceding aspects, where the angle of the longitudinal axis of the first slot to the sliding plane and/or the angle of the longitudinal axis of the second slot to the sliding plane is adjustable.

27. The intra-oral mandibular advancement device according to any one of the preceding aspects, including at least one of
(i) an upper band portion (7120) between two upper gutter portions on the upper splint; or
(ii) a lower band (7220) between two lower gutter portions on the lower splint.

28. The intra-oral device according to aspect 27, wherein the upper band portion and/or lower band portion each comprise(s) a rounded edge on at least one of the top or bottom edge(s).

29. The intra-oral device according to aspect 28, wherein the rounded edge(s) comprise a drop shape.

30. The intra-oral device according to any one of aspects 27 to 29, wherein at least one of the upper band portion and lower band portion is inclined to follow the angle of the patient's incisors.

31. The intra-oral device according to any one of the preceding aspects, wherein the lower splint connection point is located in a wing structure (7240) with a wing base (7242) extending laterally from the lower gutter portion.

32. The intra-oral device according to aspect 31, wherein the wing structure comprises a filled portion (7243) connecting the laterally extending wing base to the respective portion of the lower gutter portion, the filled portion being contoured to provide support to the cheek and to avoid dead space between the wing structure and the cheek.

33. The intra-oral device according to aspect 31 or 32, wherein the length of the wing base and of the filled portion is selected so as to avoid edges, curvatures with small radii and dead space between the wing structure and the check.

34. Method of designing an intra-oral device using computer aided design process, the computer having a processor, the processor configured to perform the method including the steps of:
obtaining an electronic image of a patient's dental arch including at least one of at least a portion of one or more of the teeth on the maxilla and at least a portion of one or more of the teeth on the mandible;
processing the received image to:
determine a retention portion or area on a crown region of at least a portion of one or more teeth available for gripping or clipping;
calculate a retention profile based on the determined retention portion or area to spread the load of retention across the at least a portion of one or more teeth available for gripping or clipping; and
design an intra-oral device having an upper splint and a lower splint and a pair of lateral connecting rods connecting the upper and lower splints,
wherein at least one of the upper splint and the lower splint includes the calculated retention profile.

35. Method according to aspect 34, wherein the retention profile is determined on the side portion of the crown region of at least a portion of one or more teeth available for gripping.

36. Method according to any one of aspects 34-35, wherein the at least a portion of the teeth available for gripping includes at least one of:
(i) the teeth between the second molar and the canines on each side of the mandible;
(ii) a plurality of teeth located between the first molar and the canines on each side of the mandible;
(iii) the teeth between the second molar and the canines on each side of the maxilla; or
(iv) a plurality of teeth located between the first molar and the canines on each side of the maxilla.

37. Method according to any one of aspects 34-36, comprising determining an undercut portion of the at least a portion of the one or more teeth and calculating an undercut portion of the profile.

38. Method according to aspect 37, wherein the undercut portion is determined on the basis of the apex (a) of the sidewall of the at least a portion of the one or more teeth and of a minimum distance to the gingival part of the at least a portion of the one or more teeth.

39. Method according to aspect 38, wherein the determination of the apex (a) is based on at least one of the direction of insertion (I) of the at least a portion of the one or more teeth into the respective gutter portion, the inserted shape of the at least a portion of the one or more teeth, or the height of the at least a portion of the one or more teeth.
40. Method according to any one of aspects 37-39, wherein the thickness (EP) of the profile is calculated on the basis of the determined undercut portion so as to provide an elastic gutter side walls adapted to clip on the at least a portion of the one or more teeth.
41. Method according to any one of aspects 34-40, wherein an inner receiving portion (7268) of the profile is located in the application position adjacent to the gingival part, the inner receiving portion (7268) being arranged at a minimum distance to the gingival part.
42. Method according to any one of aspects 34-41, further comprising manufacturing the device according to the design.
43. Method according to any one of aspects 34 to 42 wherein the device is manufactured using a computer aided manufacturing technique.

Other features of the technology will be apparent from consideration of the information contained in the following detailed description, abstract, drawings and claims.

BRIEF DESCRIPTION OF THE DRAWINGS

The present technology is illustrated by way of example, and not by way of limitation, in the figures of the accompanying drawings, in which like reference numerals refer to similar elements including:

FIG. 1*a* shows a blocked airway due to the collapse of the muscles in the upper airway blocking the upper airway.

FIG. 1*b* shows how protrusion of the lower jaw expands the space behind the tongue to prevent or reduce blockage of the upper airway.

1.3 Therapy

1.3.1 Respiratory System

Figure 1:
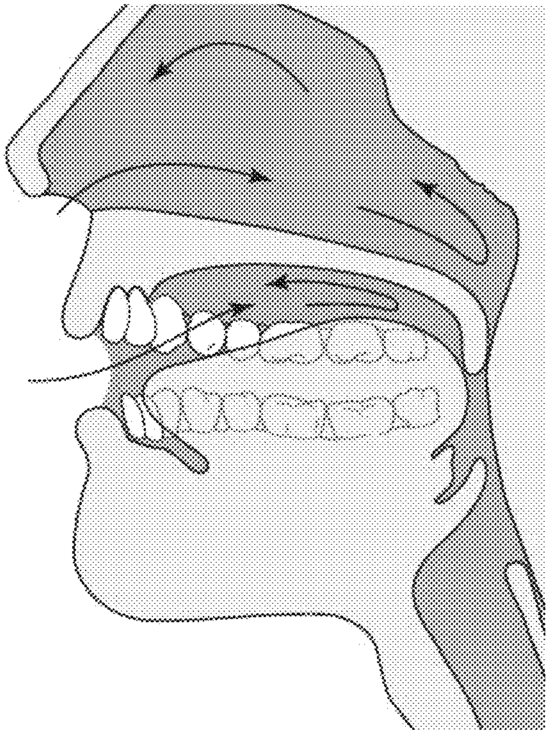
FIGS. 8*a*-1, 8*a*-2 and 8*b* through 8*e* show side views of the upper and lower splints of a Mandibular advancement device (MAD) according to the present technology.
Figure 1:
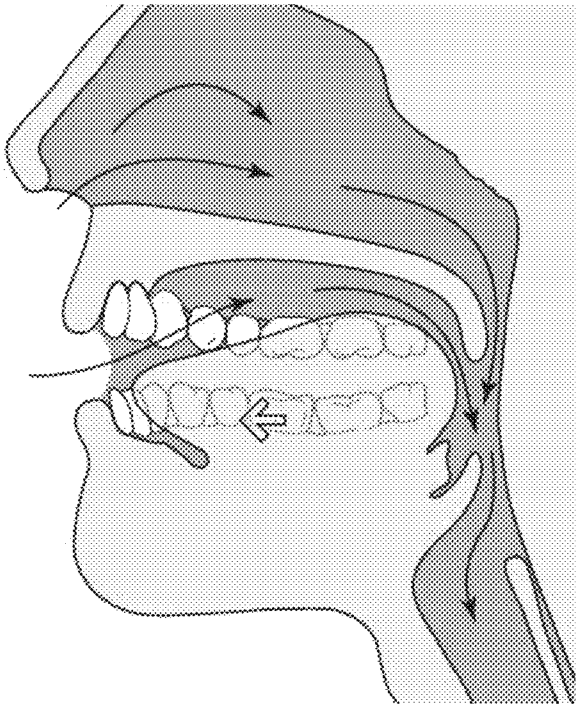

FIG. 1*a* shows a blocked airway due to the collapse of the muscles in the upper airway blocking the upper airway.

FIG. 1*b* shows how protrusion of the lower jaw expands the space behind the tongue to prevent or reduce blockage of the upper airway.

Figure 2A:
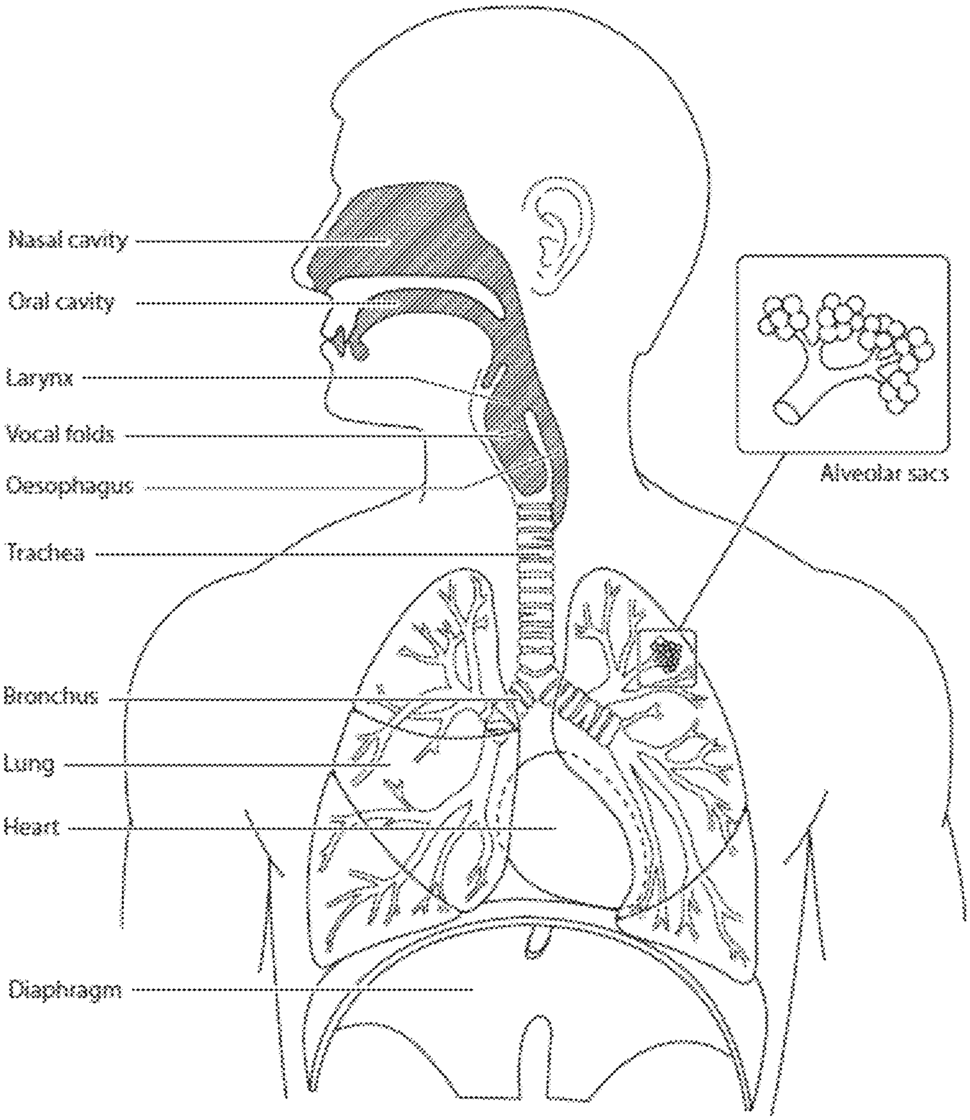
FIG. 2*a* shows an overview of a human respiratory system including the nasal and oral cavities, the larynx, vocal folds, oesophagus, trachea, bronchus, lung, alveolar sacs, heart and diaphragm.

FIG. 2*a* shows an overview of a human respiratory system including the nasal and oral cavities, the larynx, vocal folds, oesophagus, trachea, bronchus, lung, alveolar sacs, heart and diaphragm.

Figure 2B:
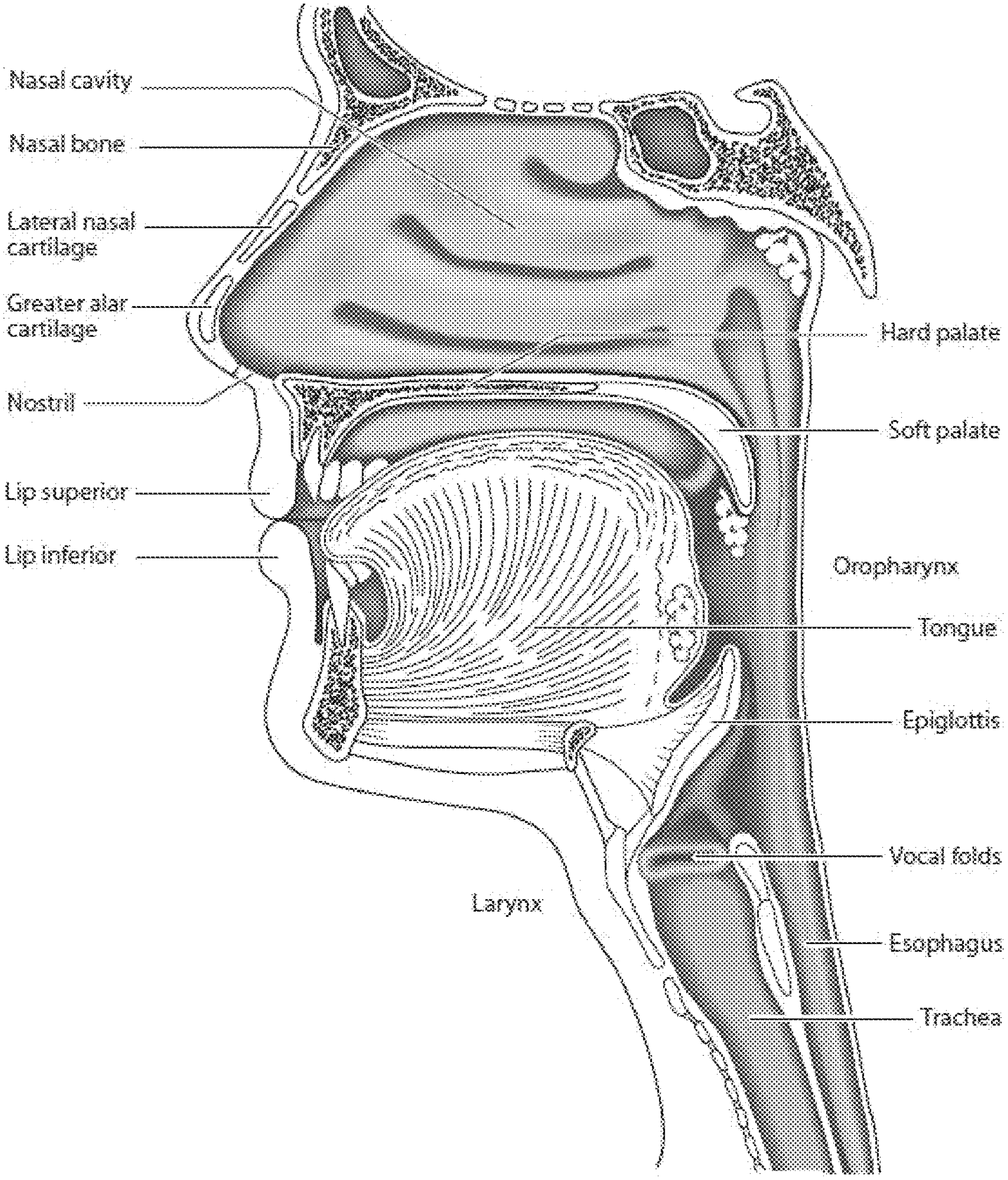
FIG. 2*b* shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

FIG. 2*b* shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

1.3.2 Mouth Anatomy

Figure 3:
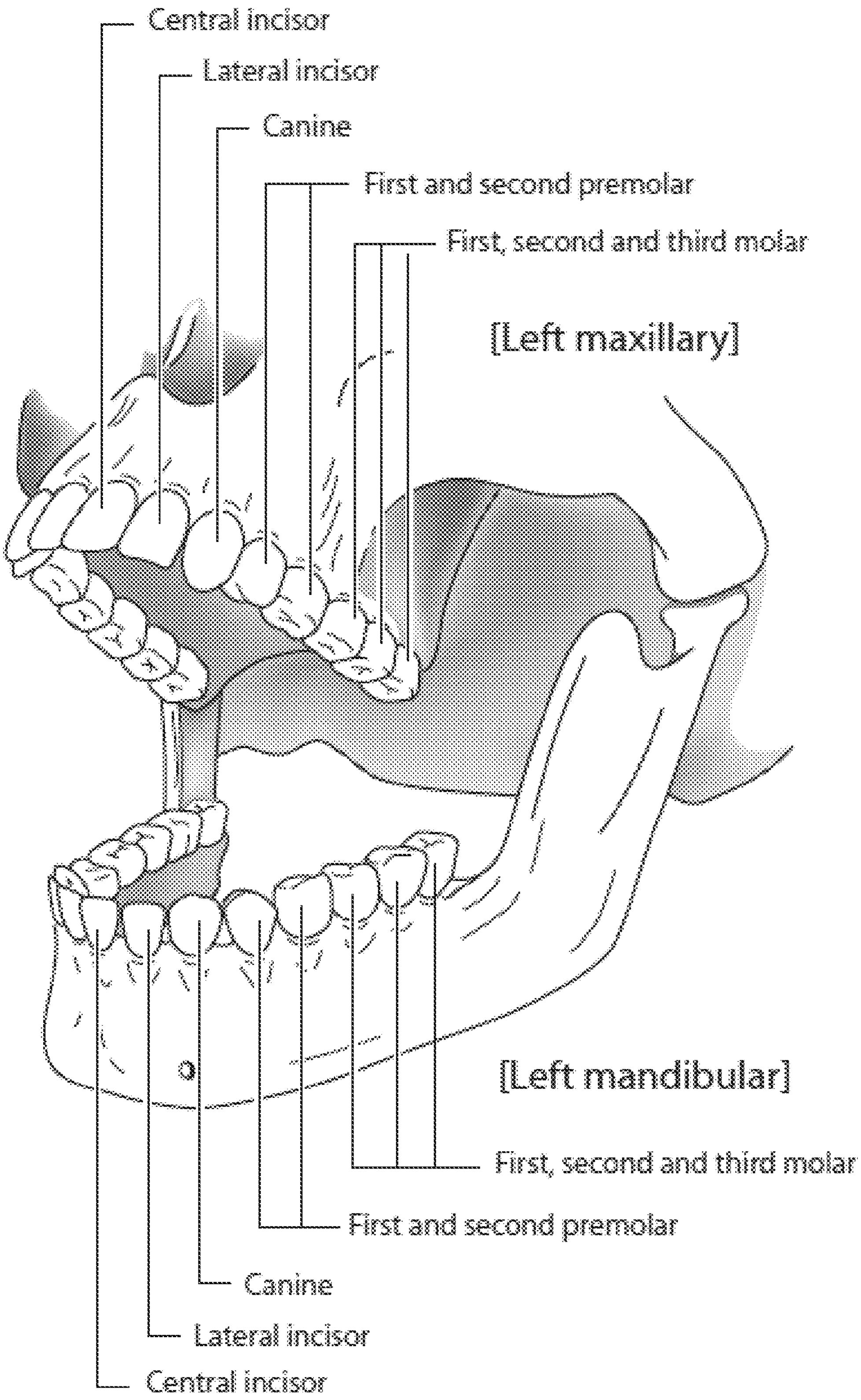
FIG. 3 shows an anterolateral view of an open human mouth showing the arrangement of the teeth on the maxilla and mandible jaws.

FIG. 3 shows an anterolateral view of an open human mouth showing the arrangement of the teeth on the maxilla and mandible jaws.

Figure 4:
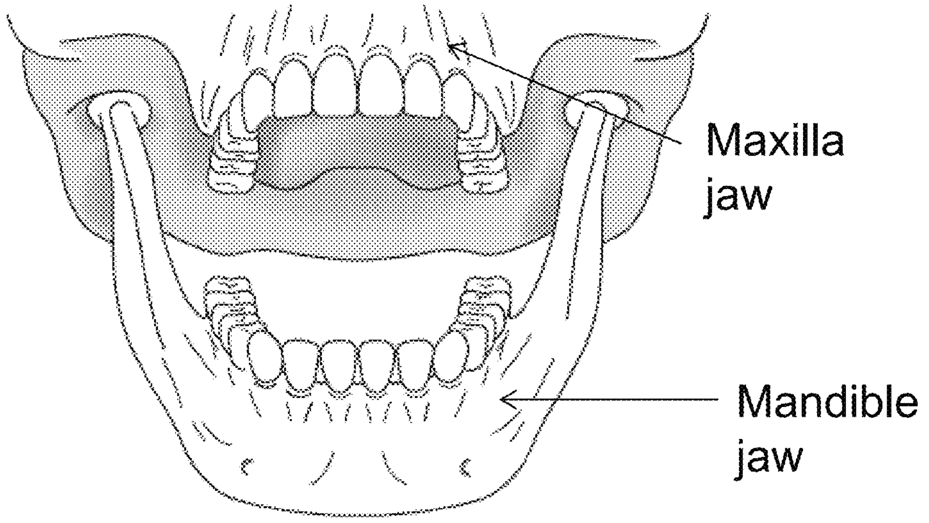
FIG. 4 shows a frontal (Antero-Posterior) view of an open human mouth showing the arrangement of the teeth on the maxilla and mandible jaws.

FIG. 4 shows a frontal (Antero-Posterior) view of an open human mouth showing the arrangement of the teeth on the maxilla and mandible jaws.

Figure 5A:
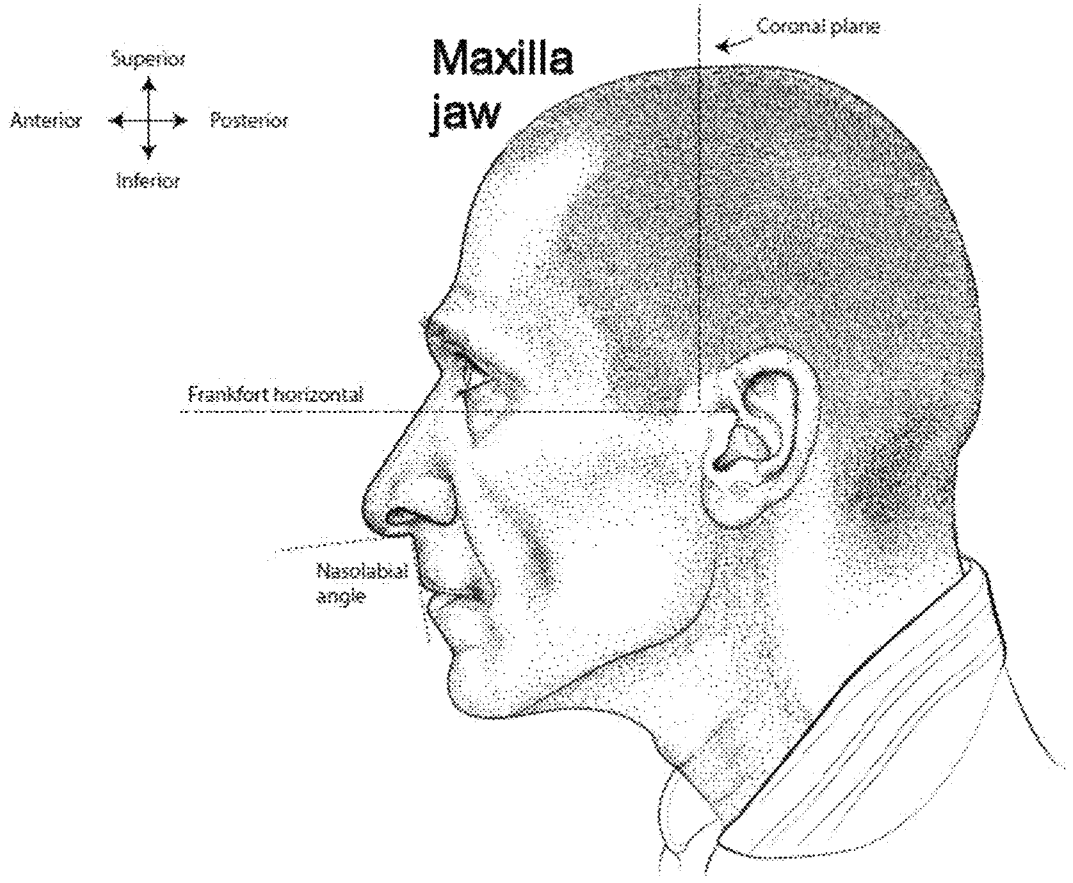
FIG. 5*a* shows a side view of a human face indicating the Frankfort horizontal plane.
Figure 5B:
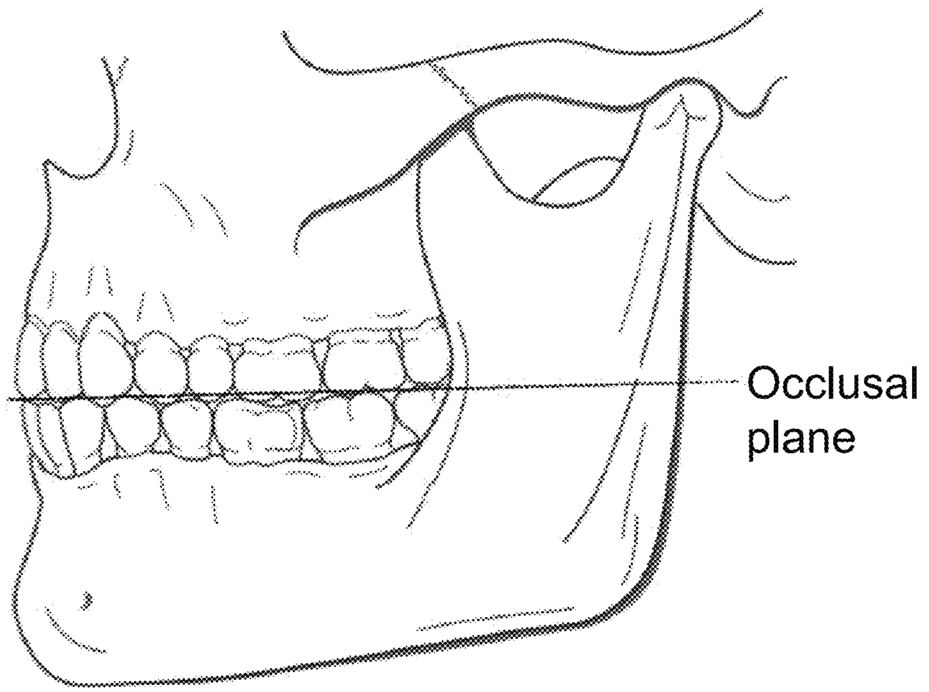
FIG. 5*b* shows an anterolateral view of a closed human mouth with a line indicating the occlusal plane.

FIG. 5*a* shows a side view of a human face indicating the Frankfort horizontal plane FIG. 5*b* shows an anterolateral view of a closed human mouth with a line indicating the occlusal plane.

1.4 Breathing Waveforms

Figure 6A:
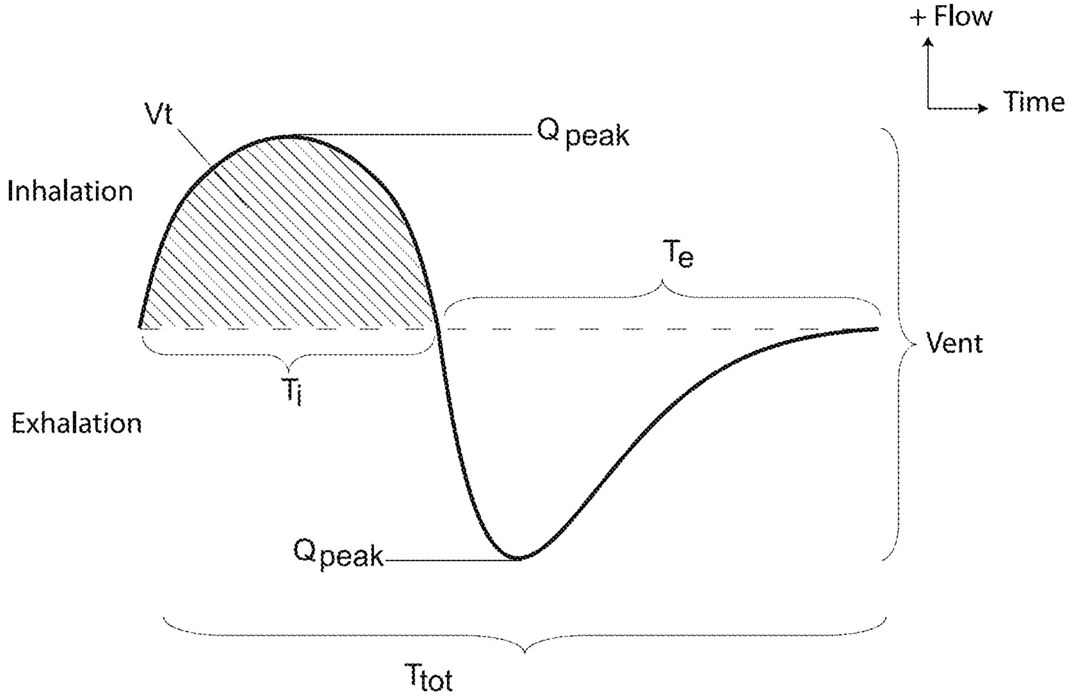
FIG. 6*a* shows a model typical breath waveform of a person while sleeping, the horizontal axis is time, and the vertical axis is respiratory flow.
Figure 6:
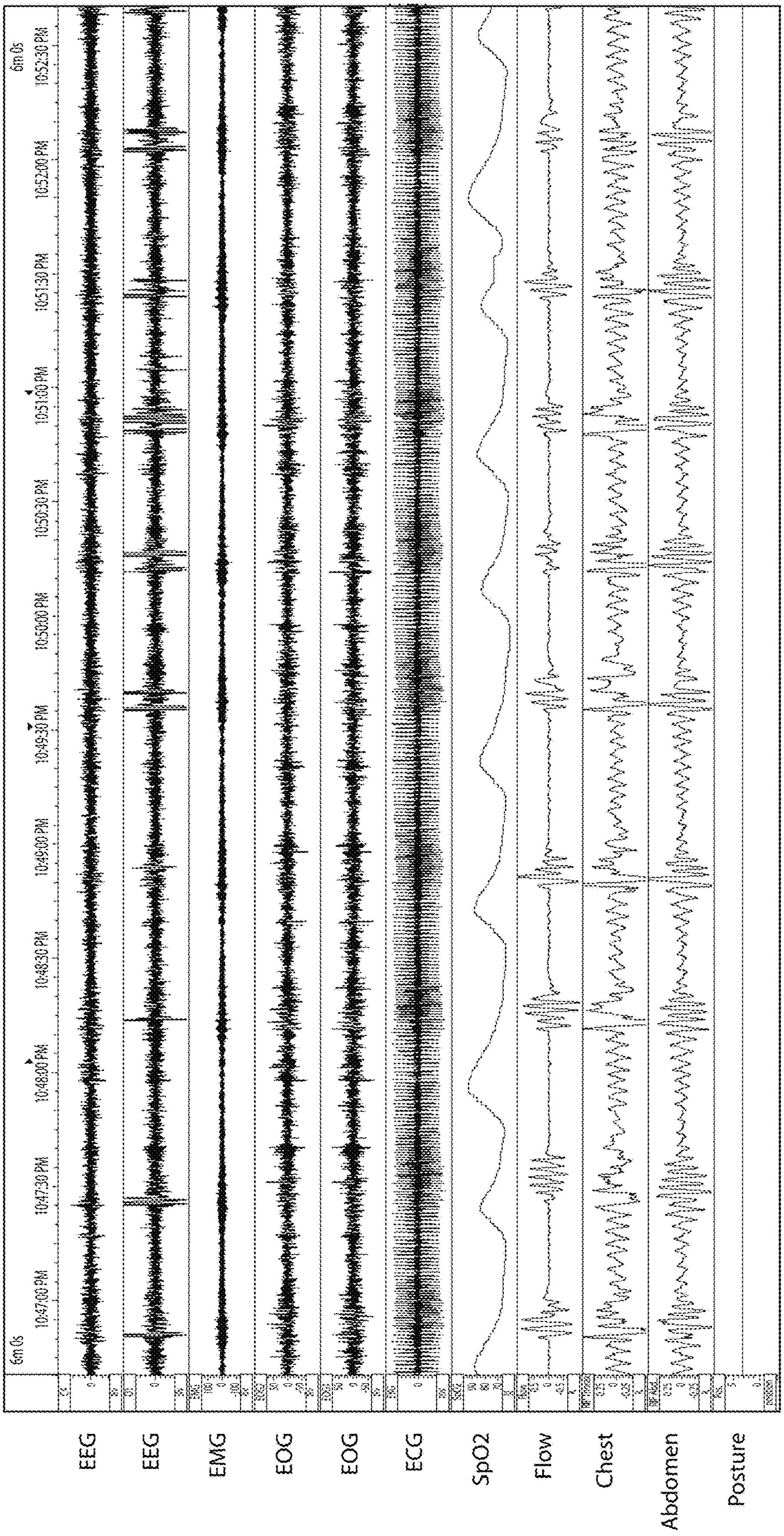
FIG. 6*b* shows polysomnography of a patient before treatment.
FIG. 6*c* shows patient flow data where the patient is experiencing a series of total obstructive apneas.
FIG. 6*d* shows a scaled inspiratory portion of a breath showing a low frequency snore.

FIG. 6*a* shows a model typical breath waveform of a person while sleeping, the horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

FIG. 6*b* shows polysomnography of a patient before treatment. There are eleven signal channels from top to bottom with a 6 minute horizontal span. The top two channels both are EEG (electoencephalogram) from different scalp locations. Periodic spikes in second represent cortical arousal and related activity. The third channel down is submental EMG (electromyogram). Increasing activity around time of arousals represent genioglossus recruitment. The fourth & fifth channels are EOG (electro-oculogram). The sixth channel is an electocardiogram. The seventh channel shows pulse oximetry (SpO2) with repetitive desaturations to below 70% from about 90%. The eighth channel is respiratory airflow using nasal cannula connected to differential pressure transducer. Repetitive apneas of 25 to 35 seconds alternating with 10 to 15 second bursts of recovery breathing coinciding with EEG arousal and increased EMG activity. The ninth shows movement of chest and tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

Figure 6C:
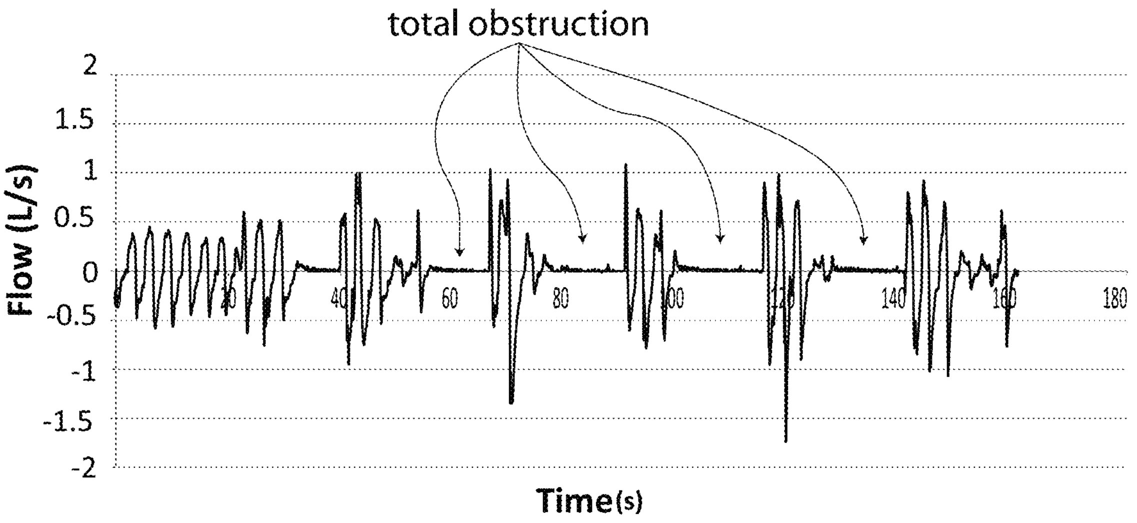

FIG. 6*c* shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

Figure 6D:
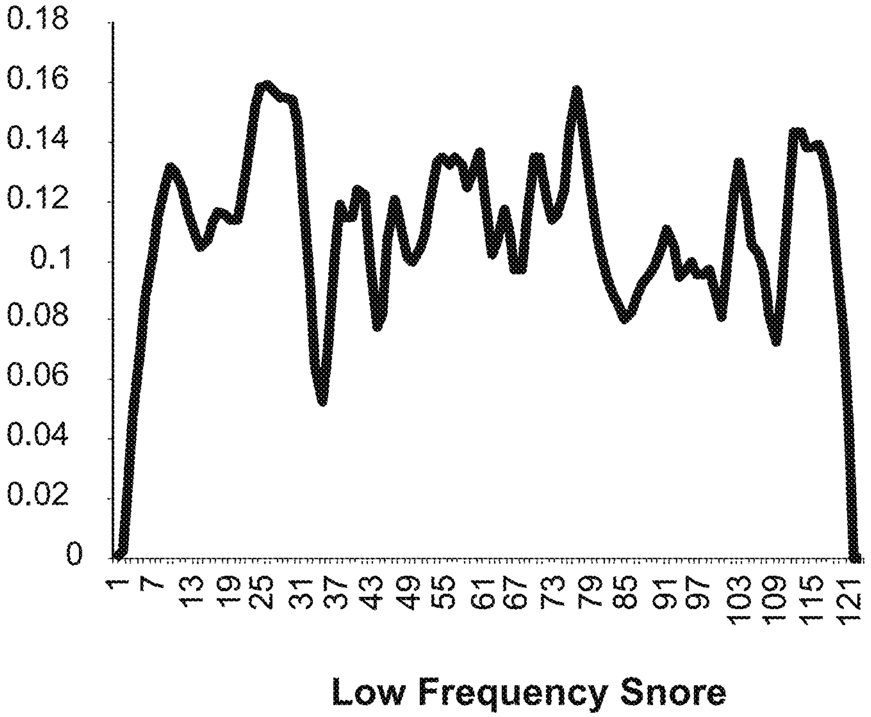

FIG. 6*d* shows a scaled inspiratory portion of a breath showing a low frequency snore.

1.5 Intra-Oral Device

FIGS. 7*a* to *f* show an intra-oral device in front views and perspective views.

FIGS. 8*a* to *e* show side views of the upper and lower splints of a Mandibular advancement device (MAD).

Figure 9A:
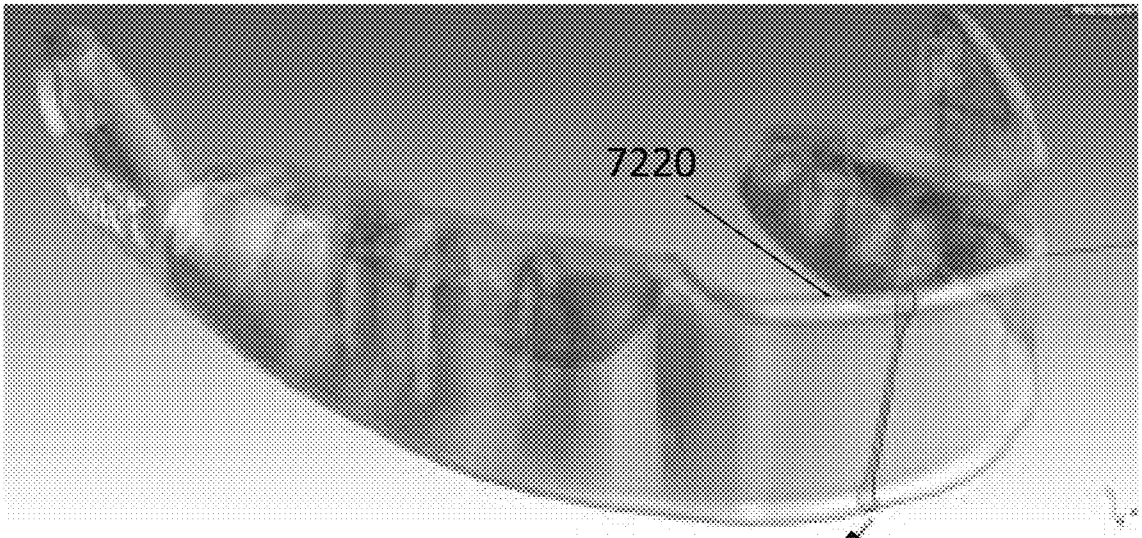
FIG. 9*a* shows an inclined mandible band portion of a lower splint according to the present technology.

FIG. 9*a* shows an inclined mandible band portion of a lower splint.

Figure 9B:
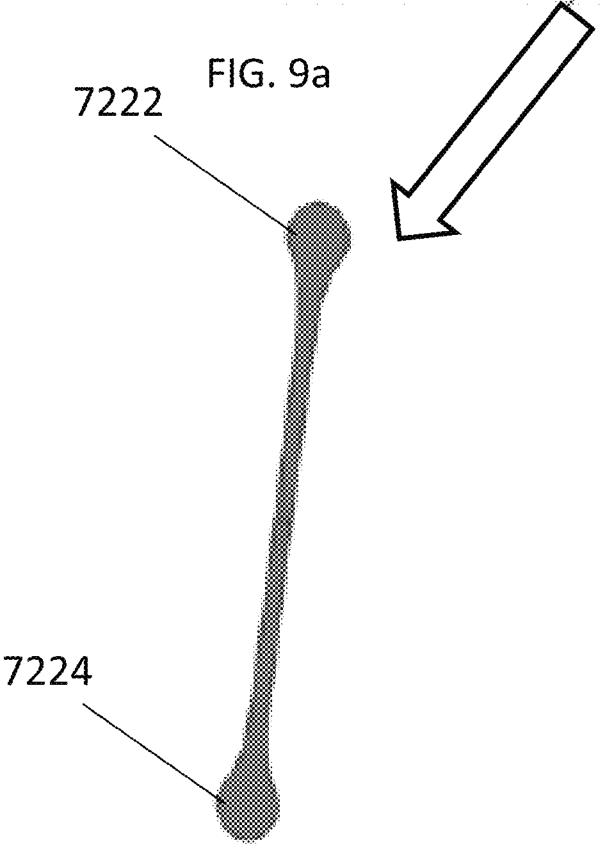
FIG. 9*b* shows the profile of the mandible band portion respectively of an MAD according to the present technology.

FIG. 9*b* shows the profile of the mandible band portion respectively of an MAD.

Figure 10A:
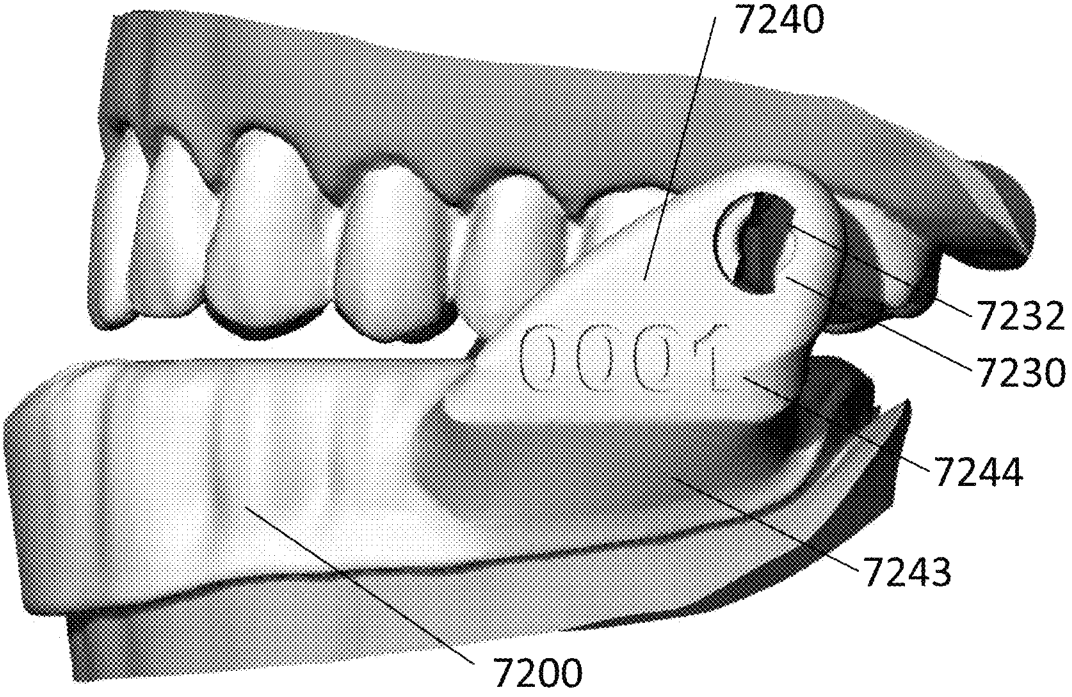
FIGS. 10*a* and 10*b* show side views of a lower splint of an MAD according to the present technology.
Figure 10B:
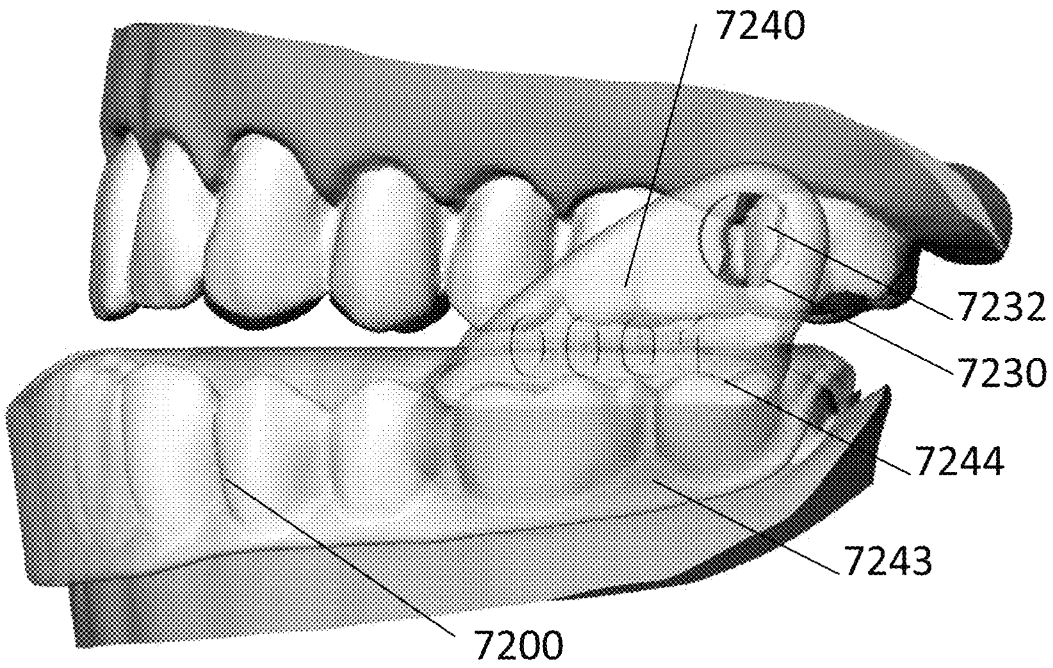

FIGS. 10*a* and 10*b* show side views of a lower splint of an MAD.

Figure 10C:
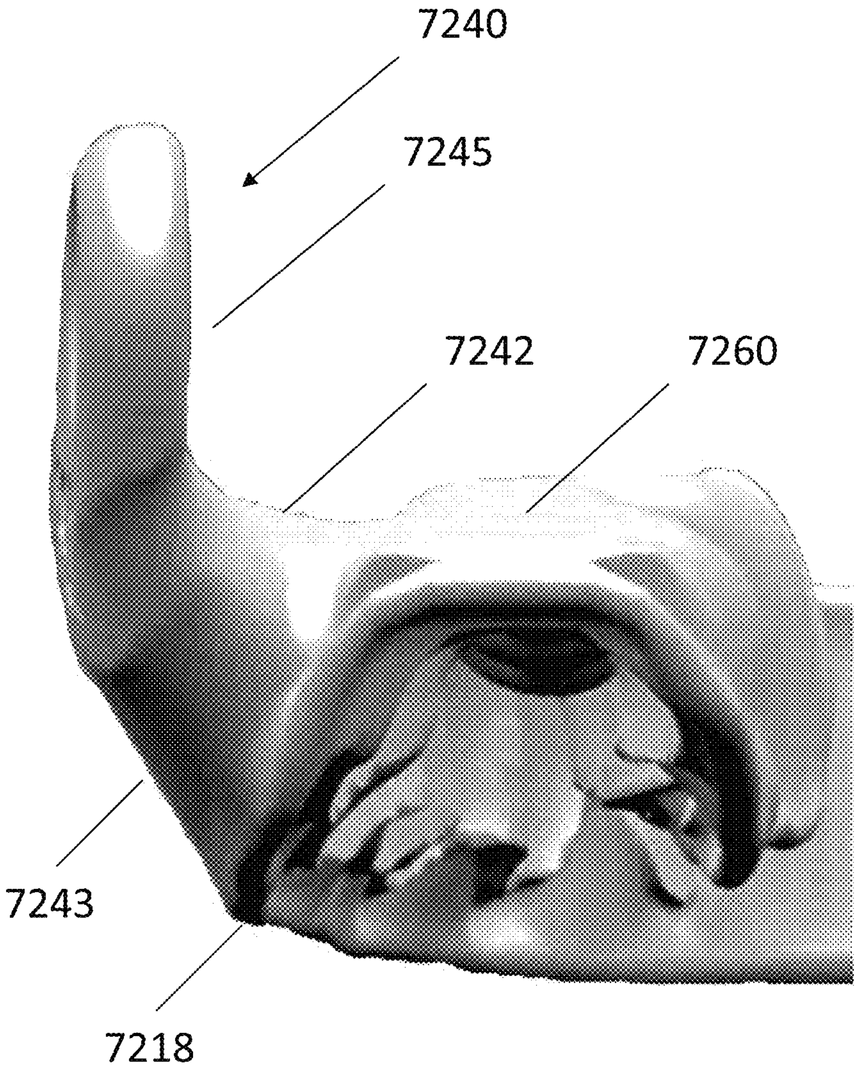
FIG. 10*c* shows a back view of a lower splint according to the present technology.

FIG. 10*c* shows a back view of a lower splint.

Figure 10D:
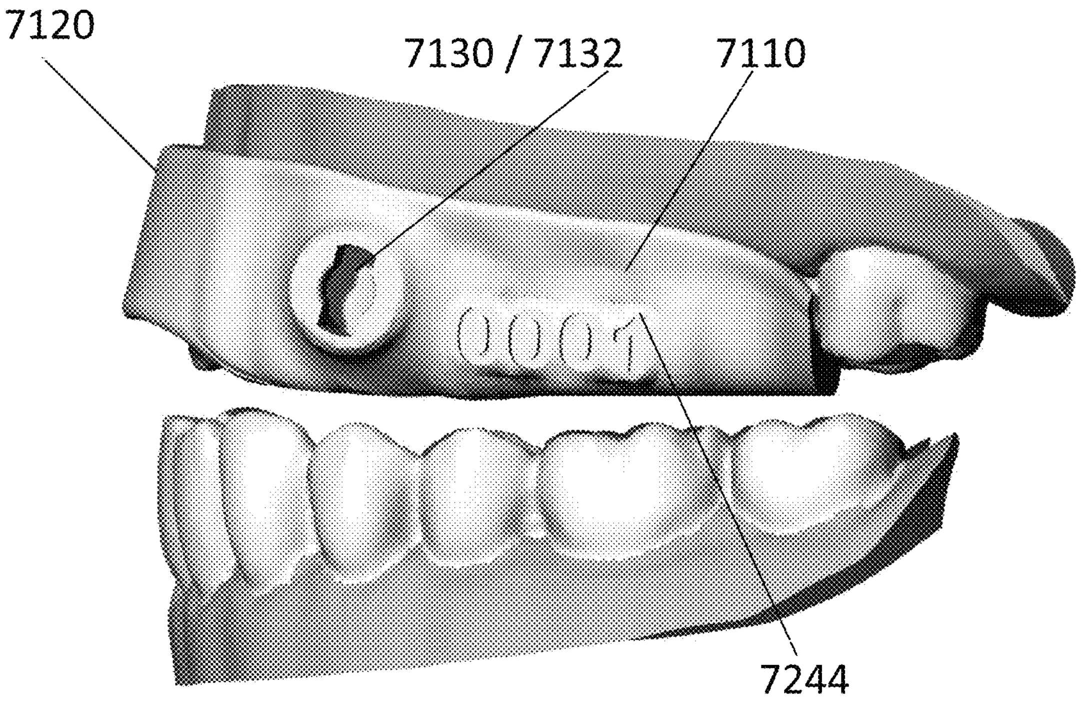
FIG. 10*d* shows a side view of an upper splint according to the present technology.

FIG. 10*d* shows a side view of an upper splint.

Figure 10E:
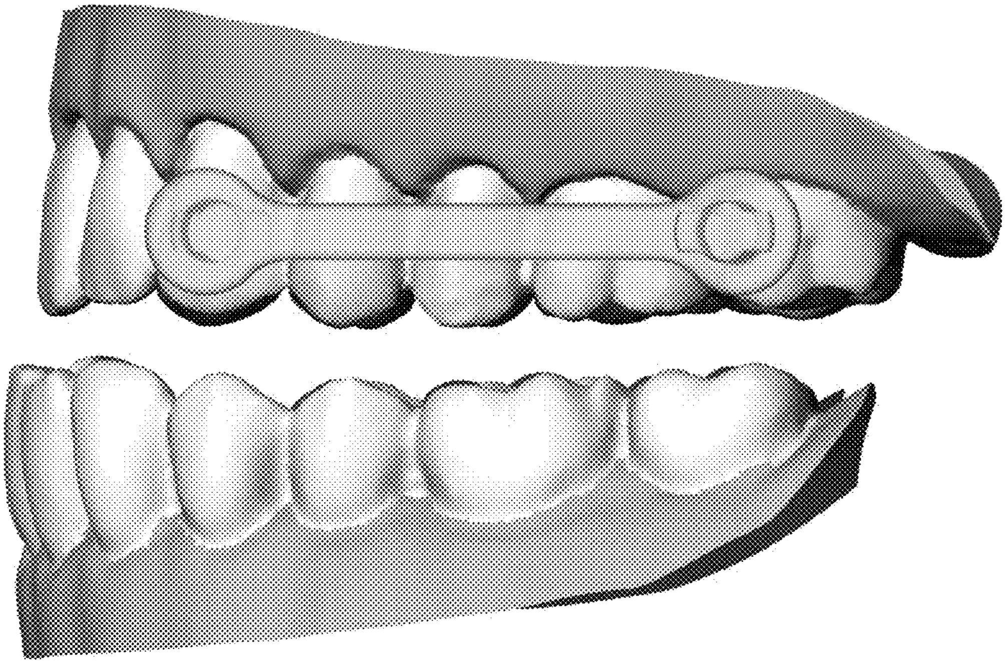
FIG. 10*e* shows a side view of a connecting rod according to the present technology.

FIG. 10*e* shows a side view of a connecting rod.

Figure 10F:
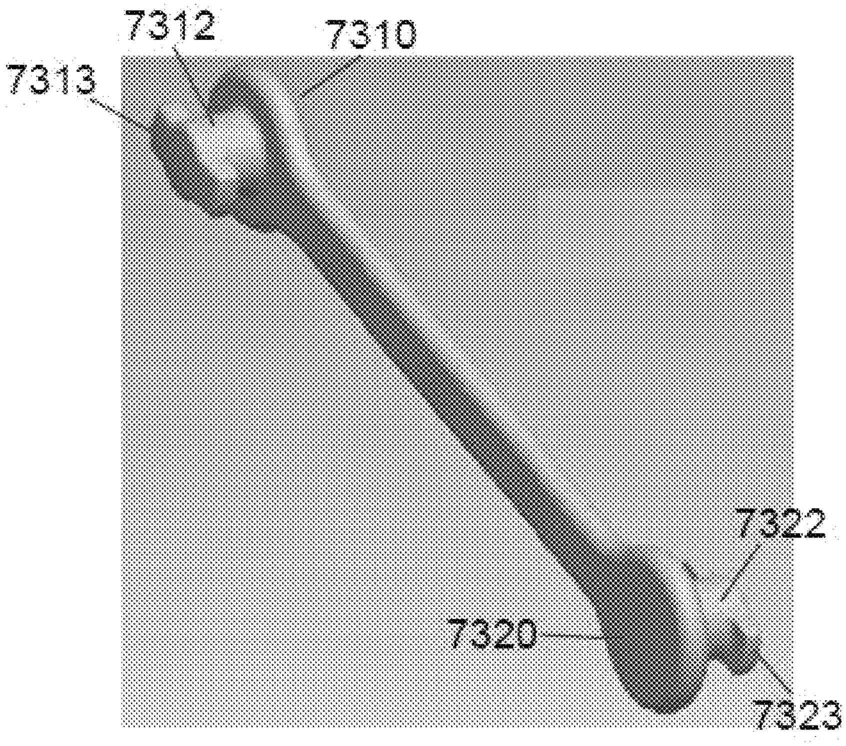
FIG. 10*f* shows a perspective view of a connecting rod according to the present technology.

FIG. 10*f* shows a perspective view of a connecting rod.

Figure 11A:
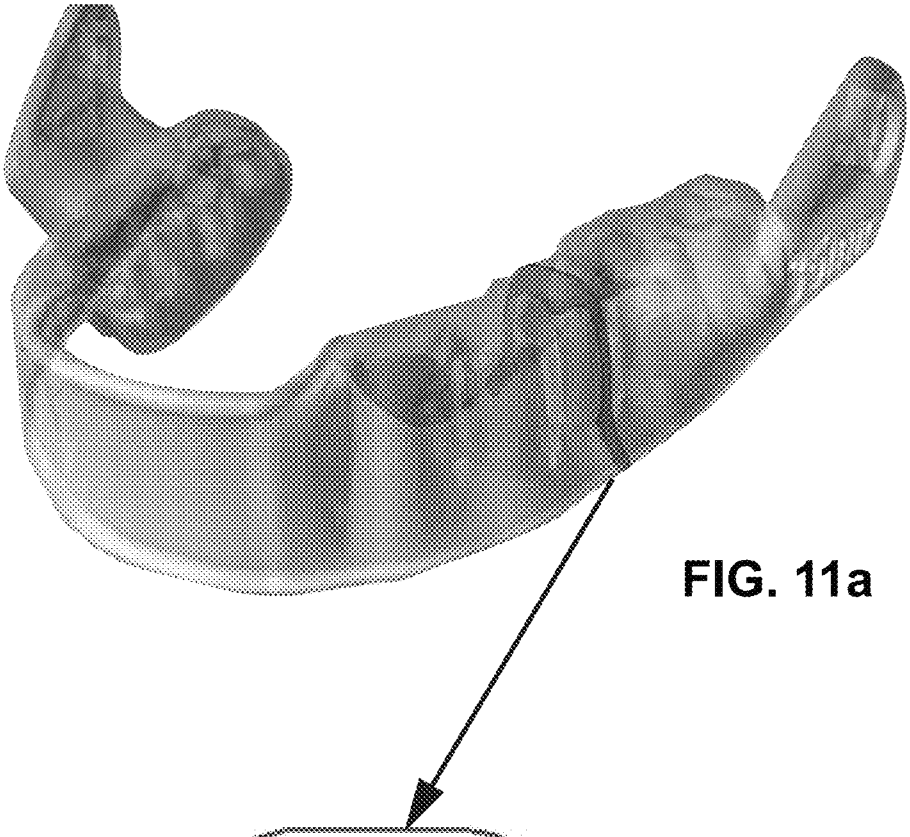
FIG. 11*a* shows a perspective view of a lower splint according to the present technology.

FIG. 11*a* shows a perspective view of a lower splint.

Figure 11B:
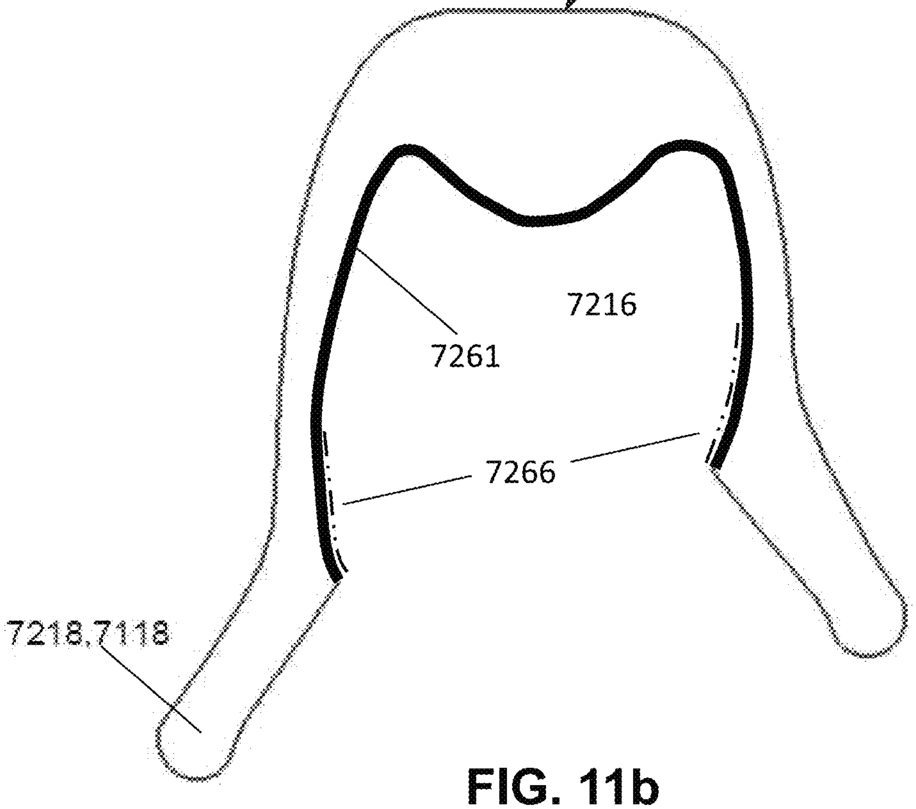
FIG. 11*b* shows a cross section of the mandible gutter portion shown in FIG. 11*a* according to the present technology.

FIG. 11*b* shows a cross section of the mandible gutter portion shown in FIG. 11*a.*

Figure 12A:
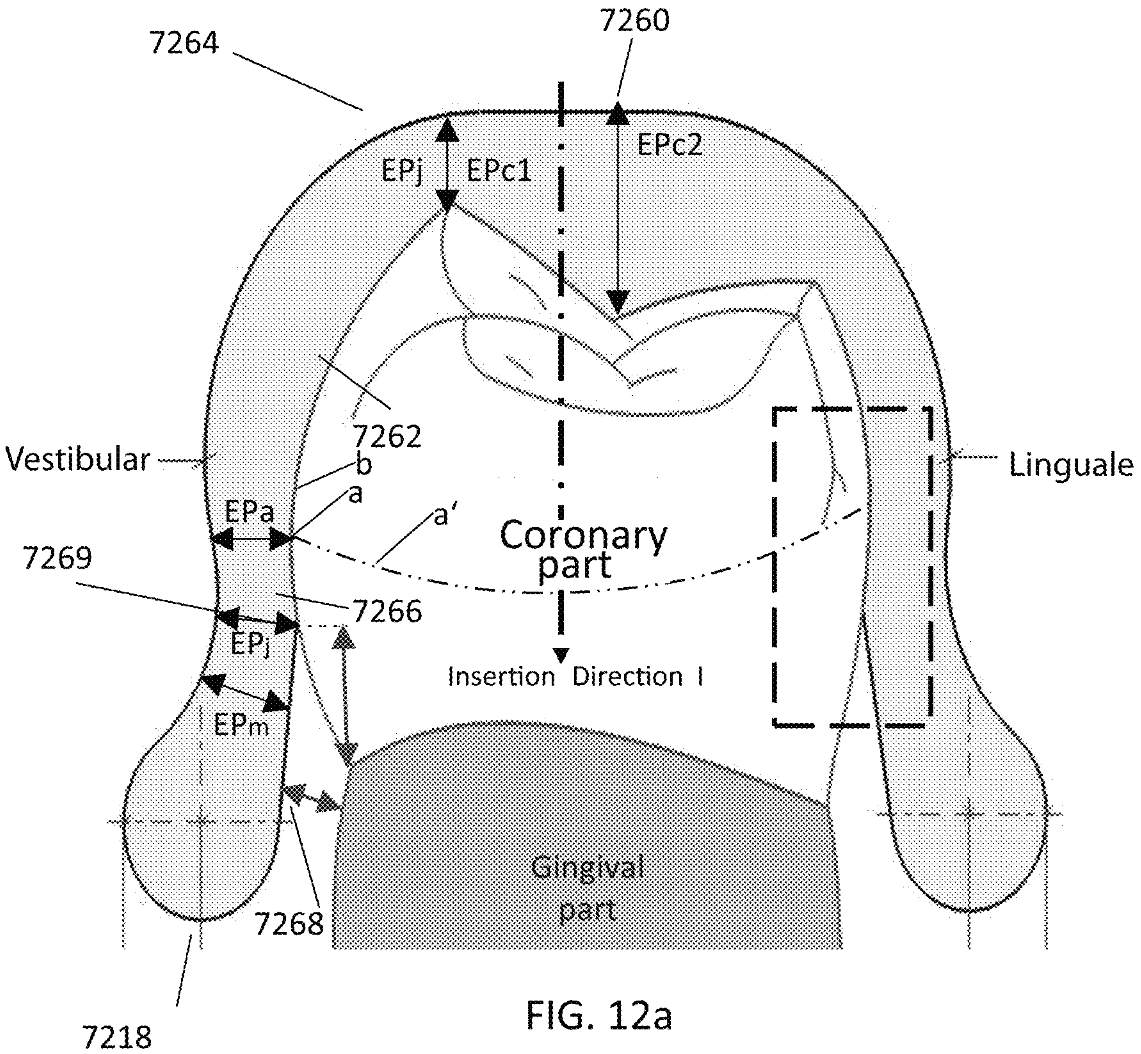
FIG. 12*a* shows a cross sectional view of a lower gutter portion engaged with a tooth according to the present technology.

FIG. 12*a* shows a cross sectional view of a lower gutter portion engaged with a tooth.

Figure 12B:
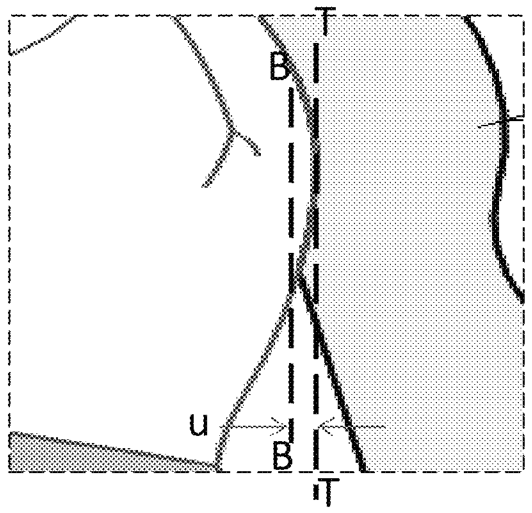
FIG. 12*b* shows an enlarged view of a part of FIG. 12*a* according to the present technology.

FIG. 12*b* shows an enlarged view of a part of FIG. 12*a.*

Figure 12C:
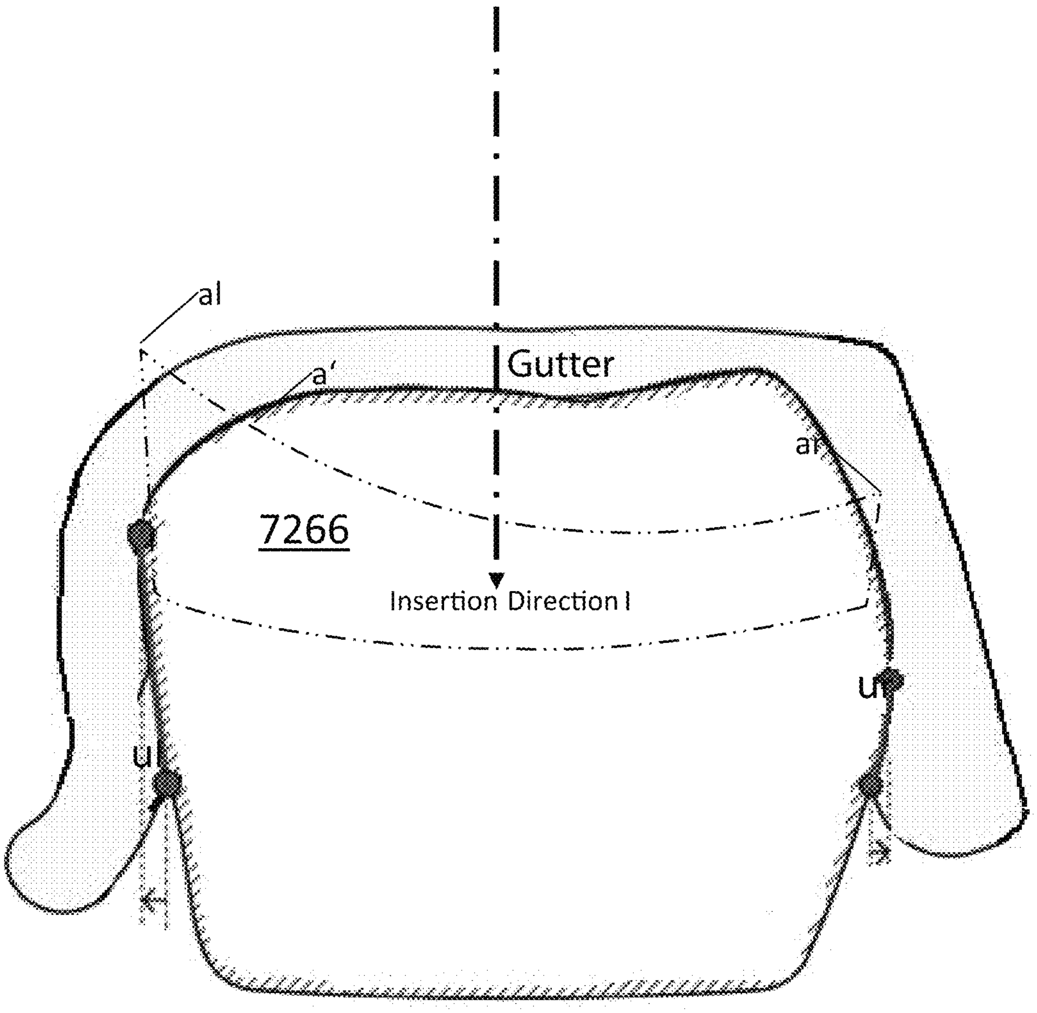
FIG. 12*c* shows another cross sectional view similar to FIG. 12*a* according to the present technology.

FIG. 12*c* shows another cross sectional view similar to FIG. 12*a.*

Figure 12D:
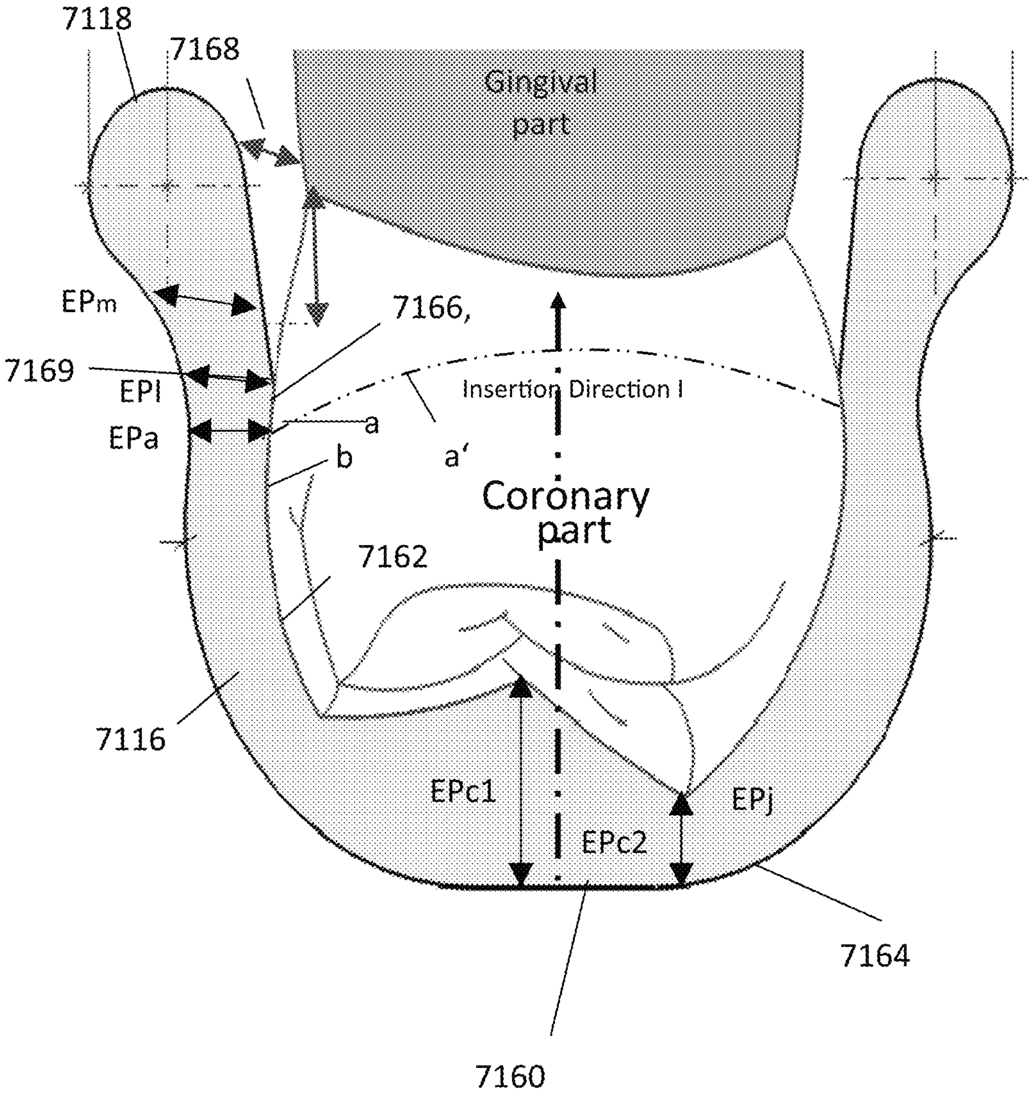
FIG. 12*d* shows a cross sectional view of an upper gutter portion engaged with a tooth according to the present technology.

FIG. 12*d* shows a cross sectional view of a upper gutter portion engaged with a tooth.

Figure 13:
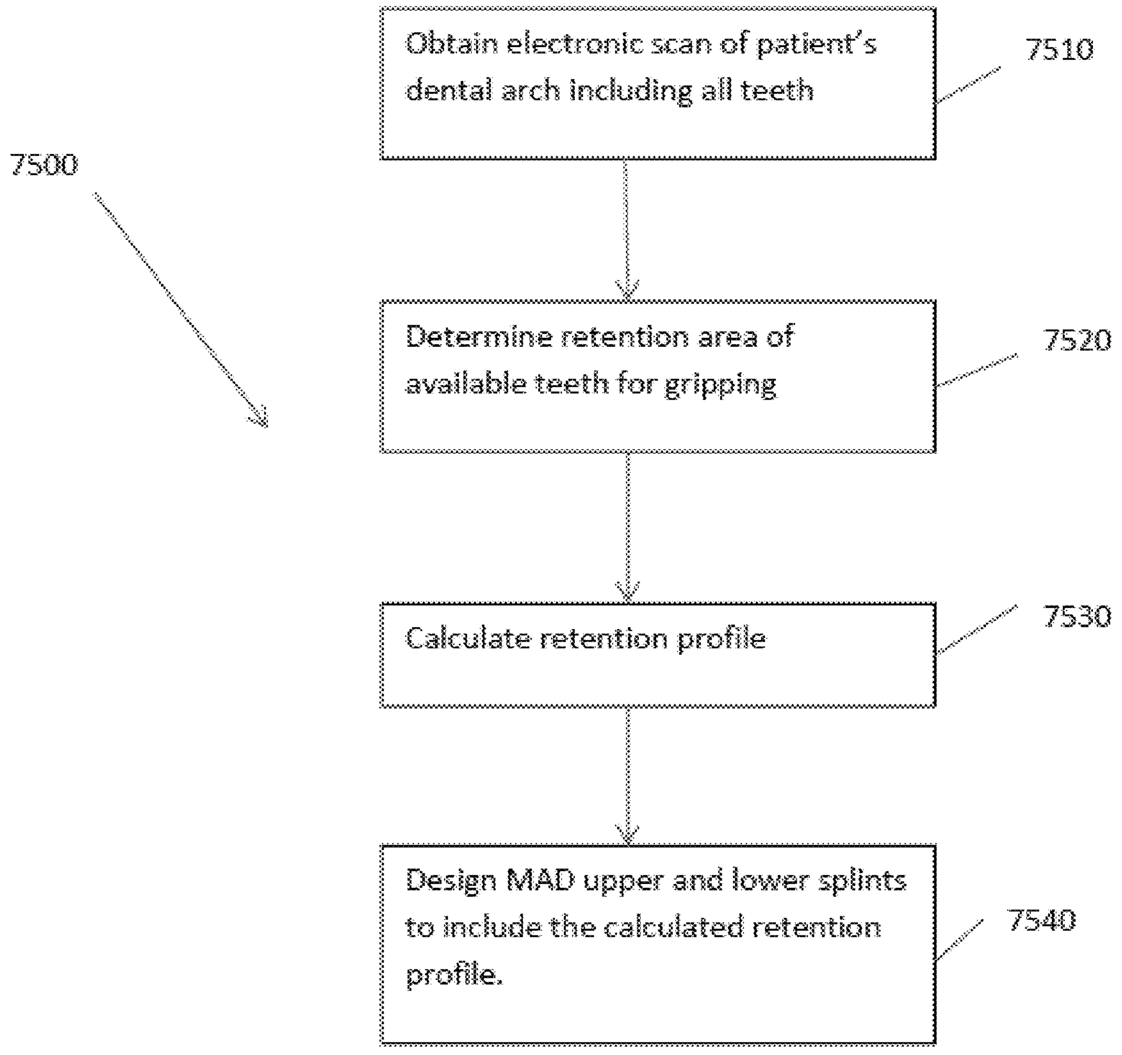
FIG. 13 shows a process for designing a MAD having improved retention using a computer aided design process according to the present technology.

FIG. 13 shows a process for designing a MAD having improved retention using a computer aided design process.

Figure 14:
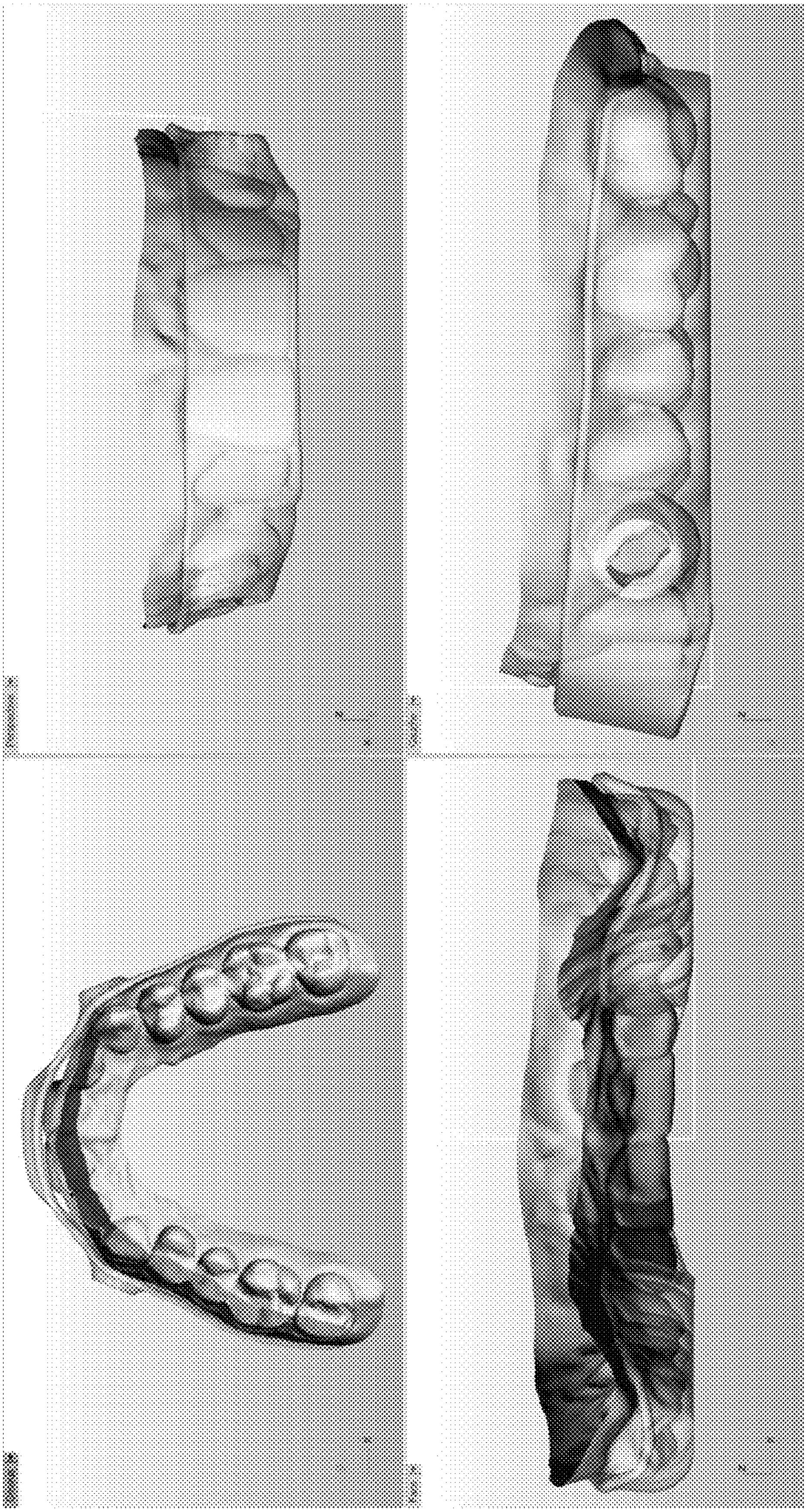
FIGS. 14*a* and 14*b* show further views of MAD according to the present technology according to the present technology.
Figure 14:
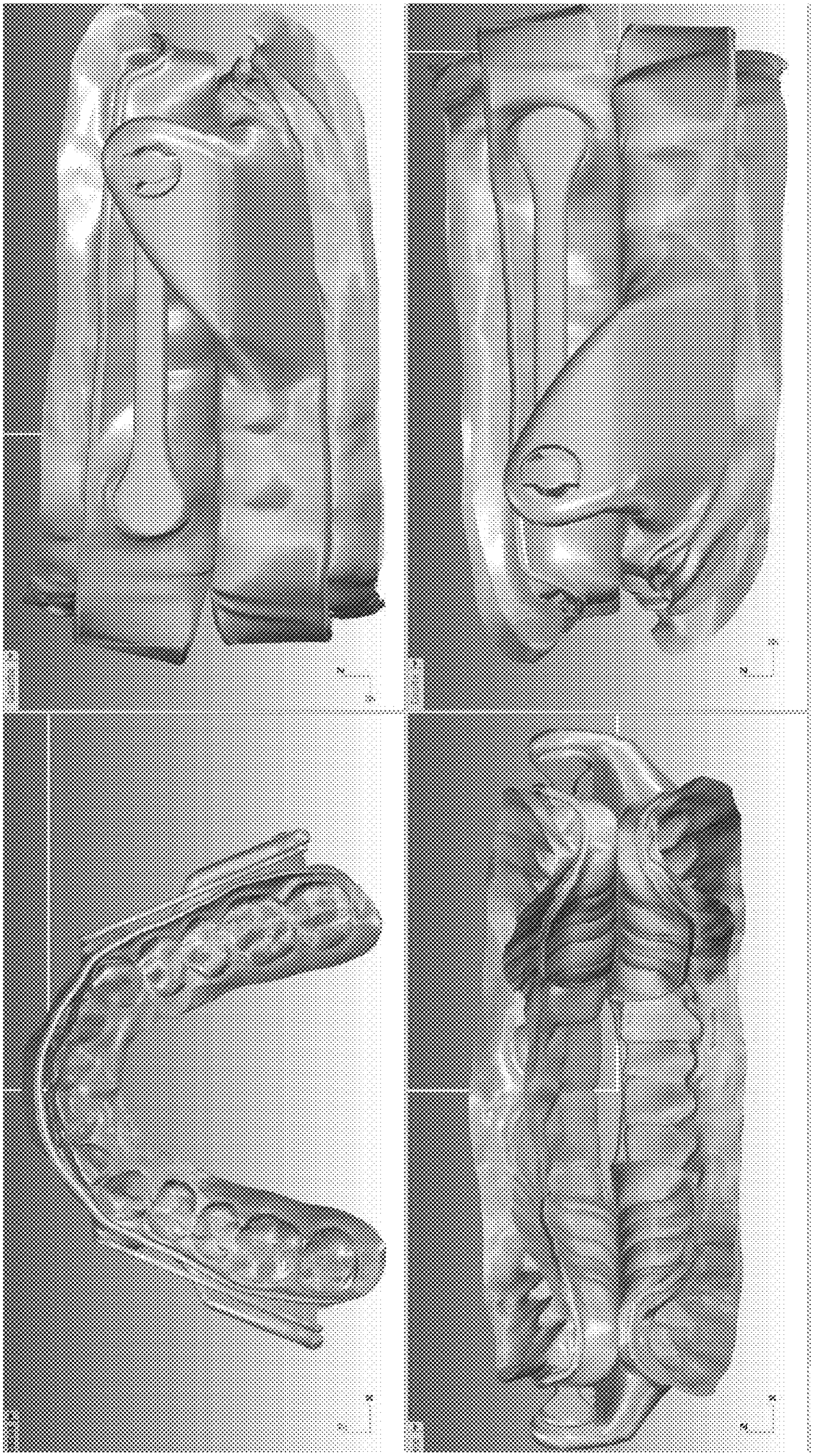
Figure 15A:
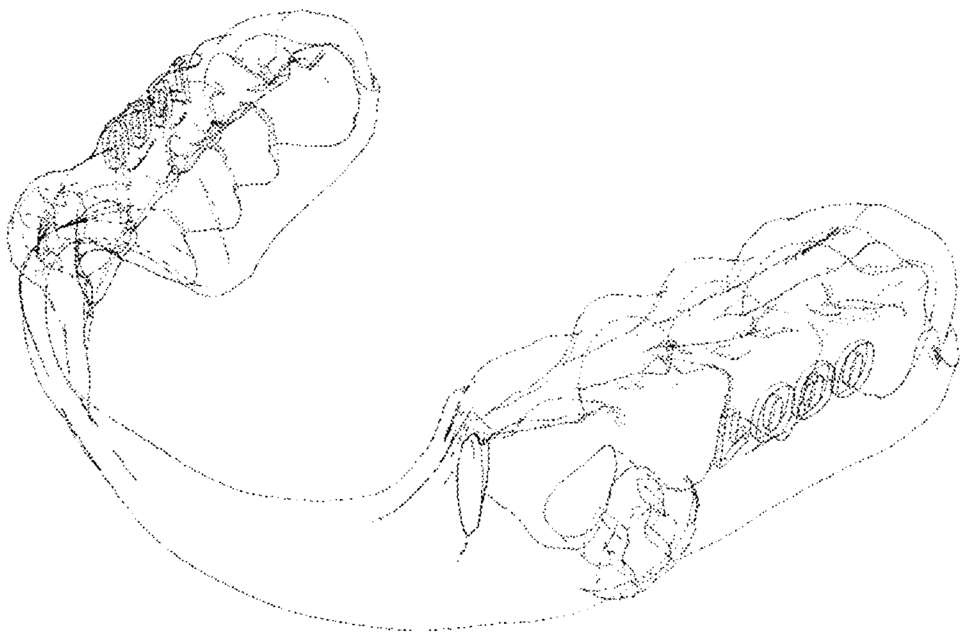
FIGS. 15*a* and 15*b* show further views of MAD according to the present technology according to the present technology.
Figure 15B:
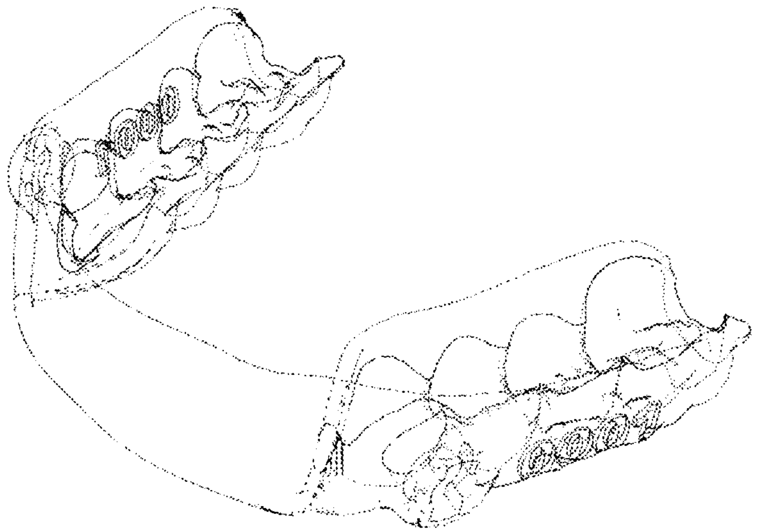

FIGS. 14 and 15 show further views of MAD according to the present technology.

DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

1.6 Intra-Oral Device 7000

Figure 7A:
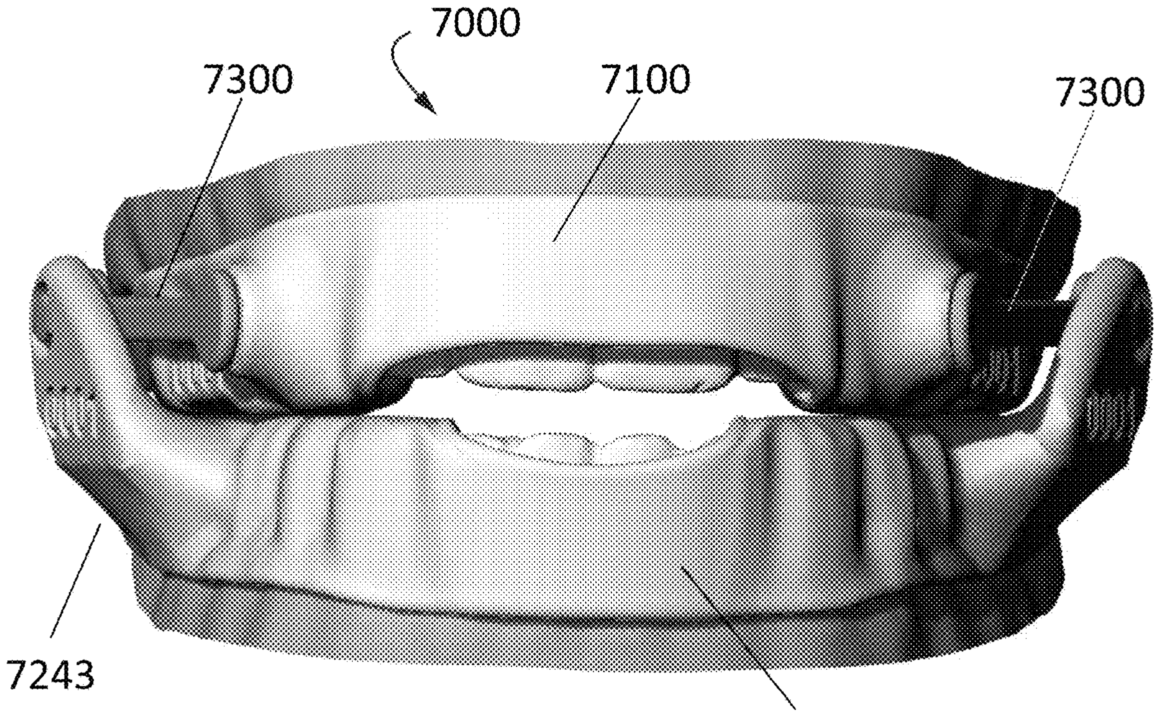
FIGS. 7*a* to 7*f* show an intra-oral device in front views and perspective views according to the present technology.
Figure 7B:
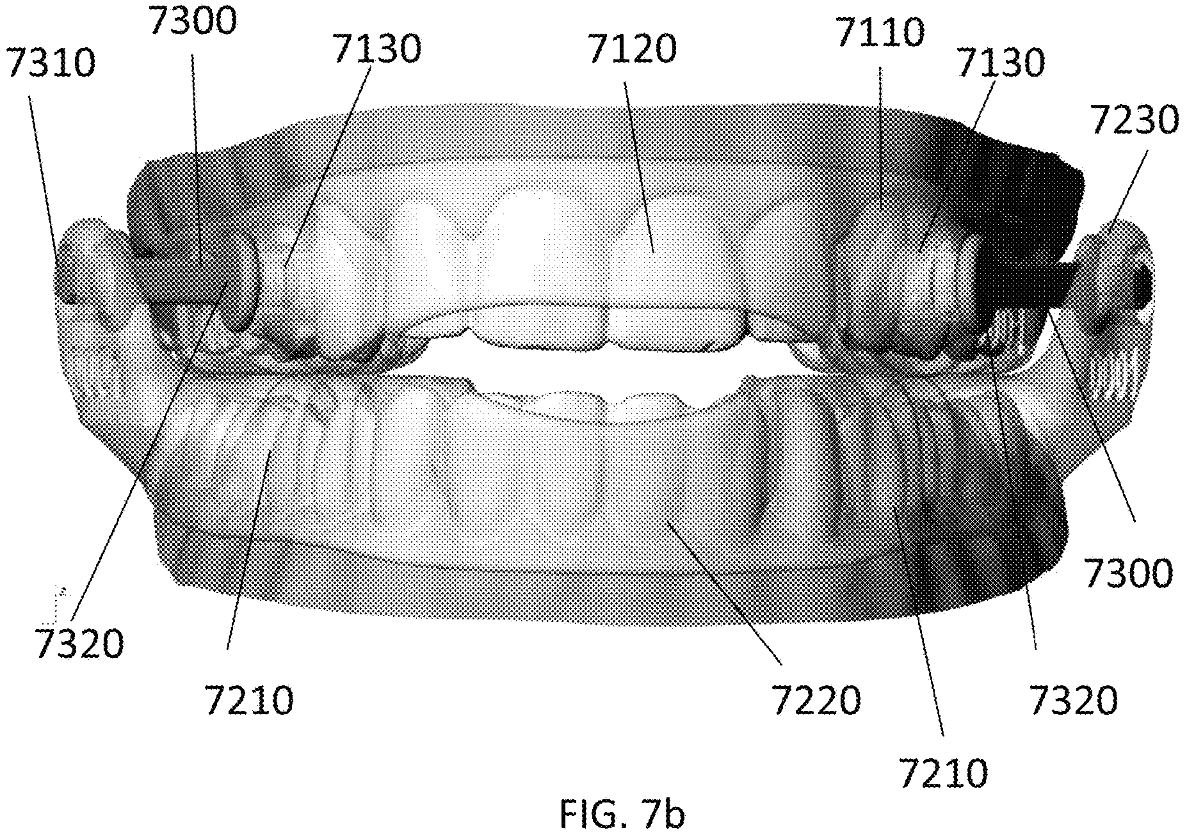
Figure 7C:
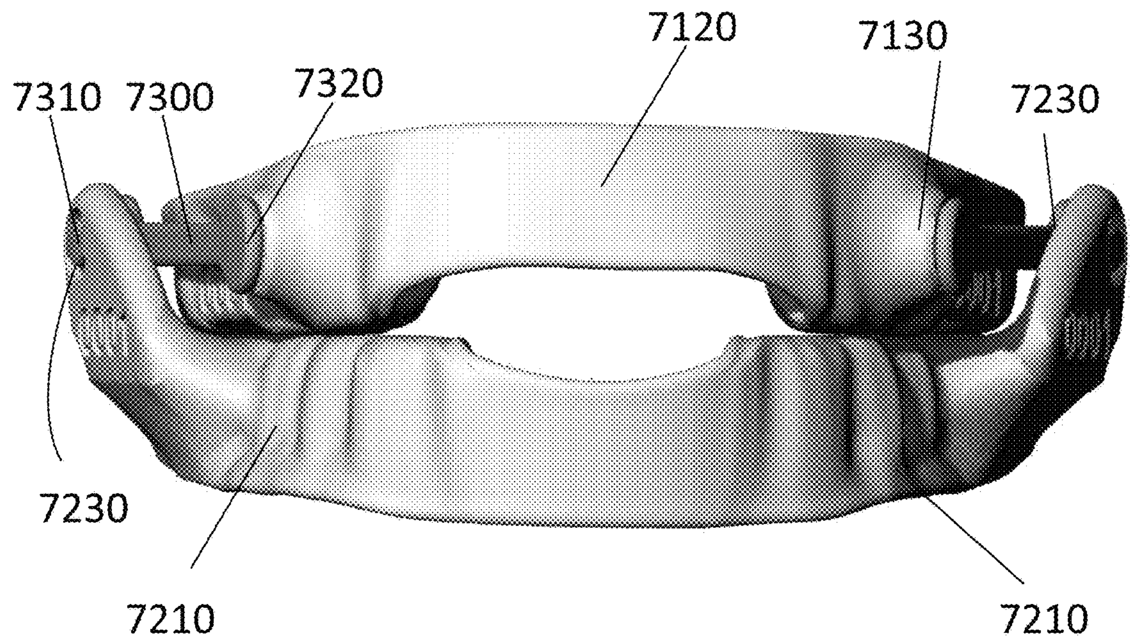
Figure 7D:
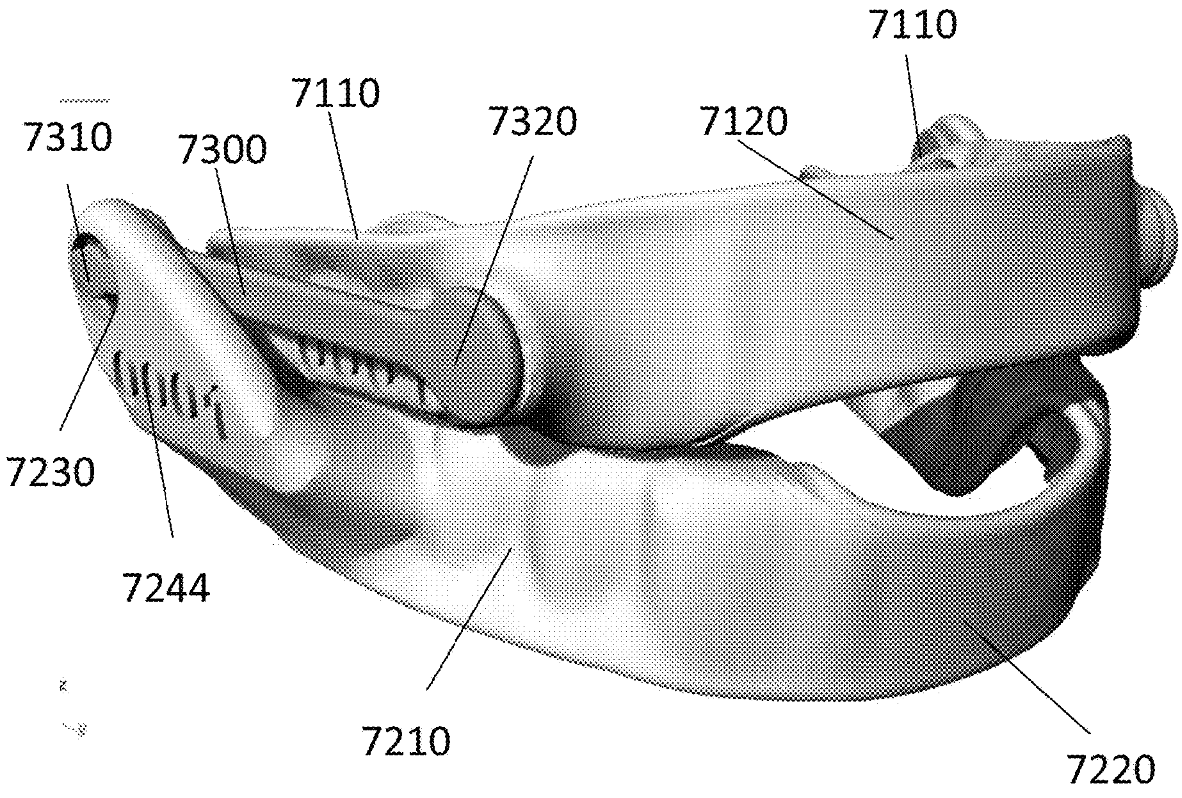
Figure 7E:
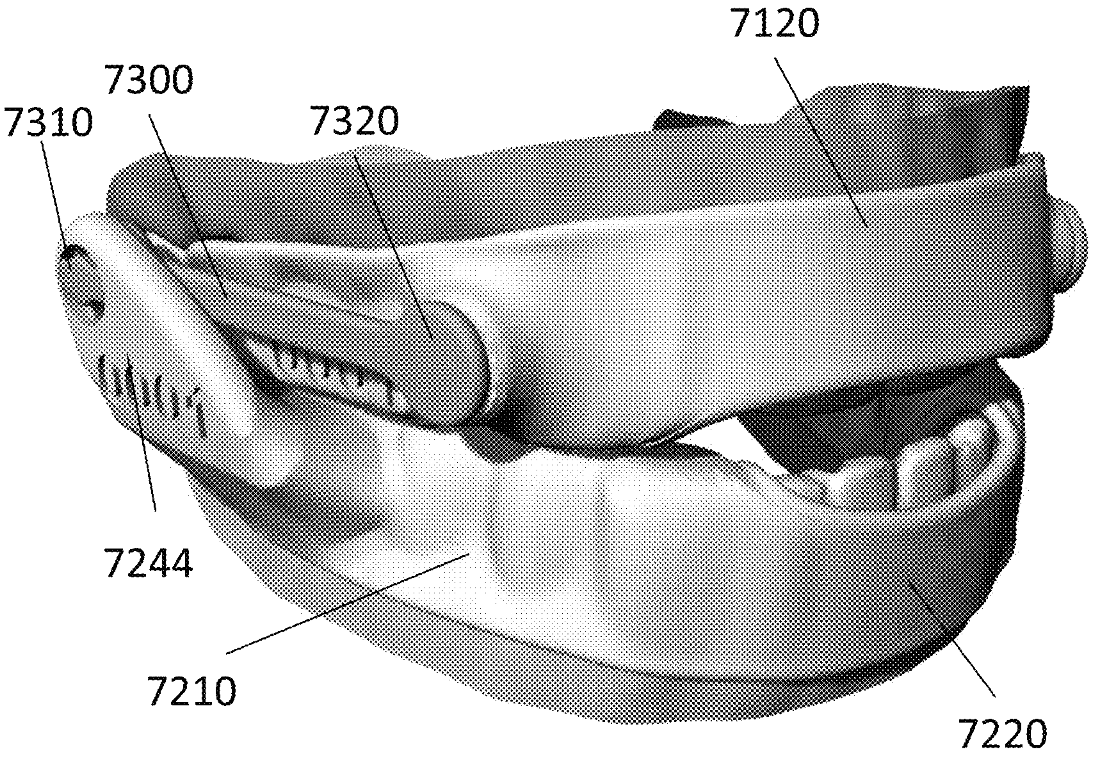
Figure 7F:
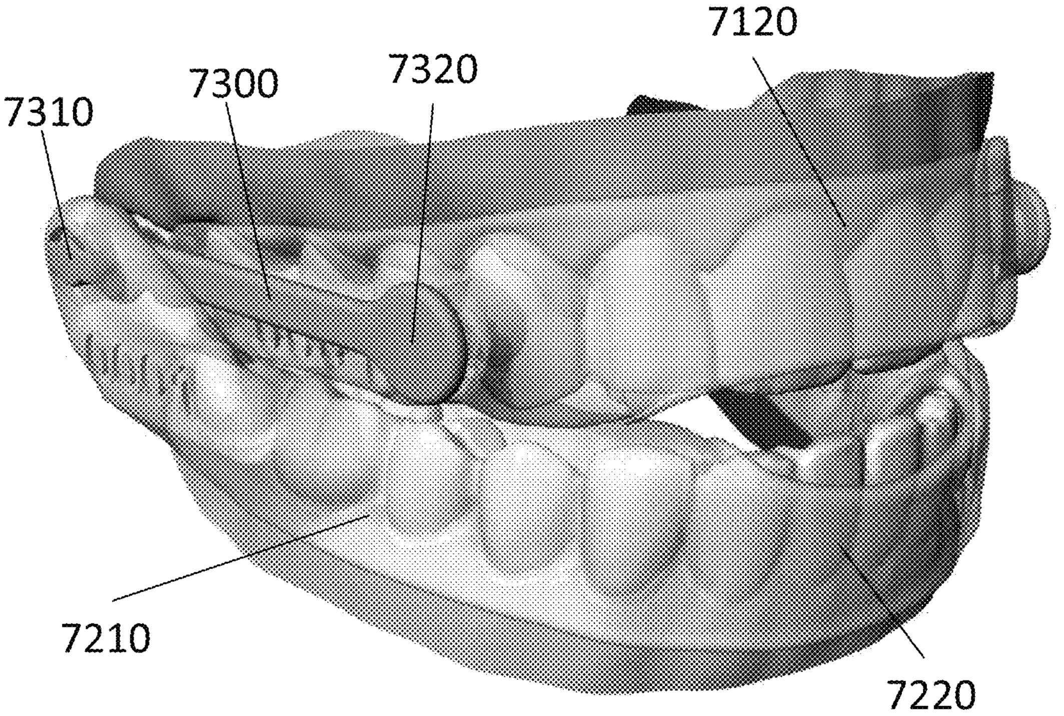

FIG. 7*a* discloses an intra-oral device or a mandibular advancement device (MAD) 7000 fitted over a mould of an upper jaw and lower jaw including teeth. The intra-oral device or MAD comprises an upper splint 7100, a lower splint 7200 and a pair of connecting rods 7300 connecting the upper and lower splints 7100, 7200 together.

As seen in FIGS. 7*a* to 8*e*, the upper splint 7100 includes two maxilla or upper gutter portions 7110 designed or structured to fit over at least a portion of one or more teeth on each side of the maxilla or upper jaw. The upper gutter portions 7110 may cover a plurality of teeth in the region between the molars and canine on the maxilla. A maxilla or upper band portion 7120 is preferably provided between the two upper gutter portions 7110 to join the two upper gutter portions 7110 together. The upper band portion 7120 may be designed to extend between the two upper gutter portions 7110 across the front portion of the lateral and central incisors and may not engage with the internal or the external surface of these incisor teeth. Here, the upper band portion 7120 reduces the visual impact of the upper splint when inserted within the patient's mouth. Preferably, the upper splint 7100 is formed as a single piece with the upper gutter portions 7110 and the upper band portion 7120 integrally formed together.

However, it is noted that the upper splint 7100 may include a single upper gutter portion 7110 designed to fit over all of the teeth of the maxilla, thus no upper band portion 7120 would be required in such an upper splint. Such an upper splint may be more intrusive within the mouth. Such an upper splint may be used when the splint is used to treat Bruxism alone or simultaneously with treating obstructive sleep apnea.

The upper splint 7100 also may include one or more, but preferably a pair of upper splint connection points 7130, preferably one on each side of the upper splint 7100, to allow connection of a respective second rod end 7320 of each one of the pair of connecting rods 7300, to the upper splint 7100.

Figures 1, 8A:
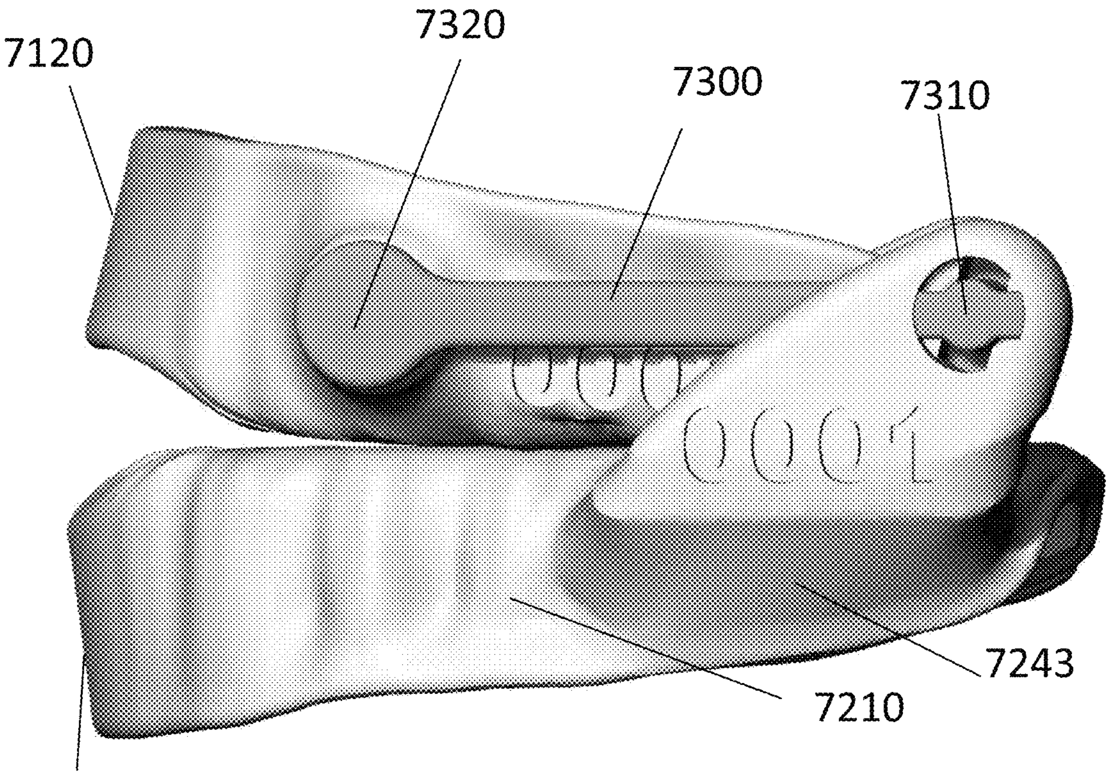
Figures 2, 8A:
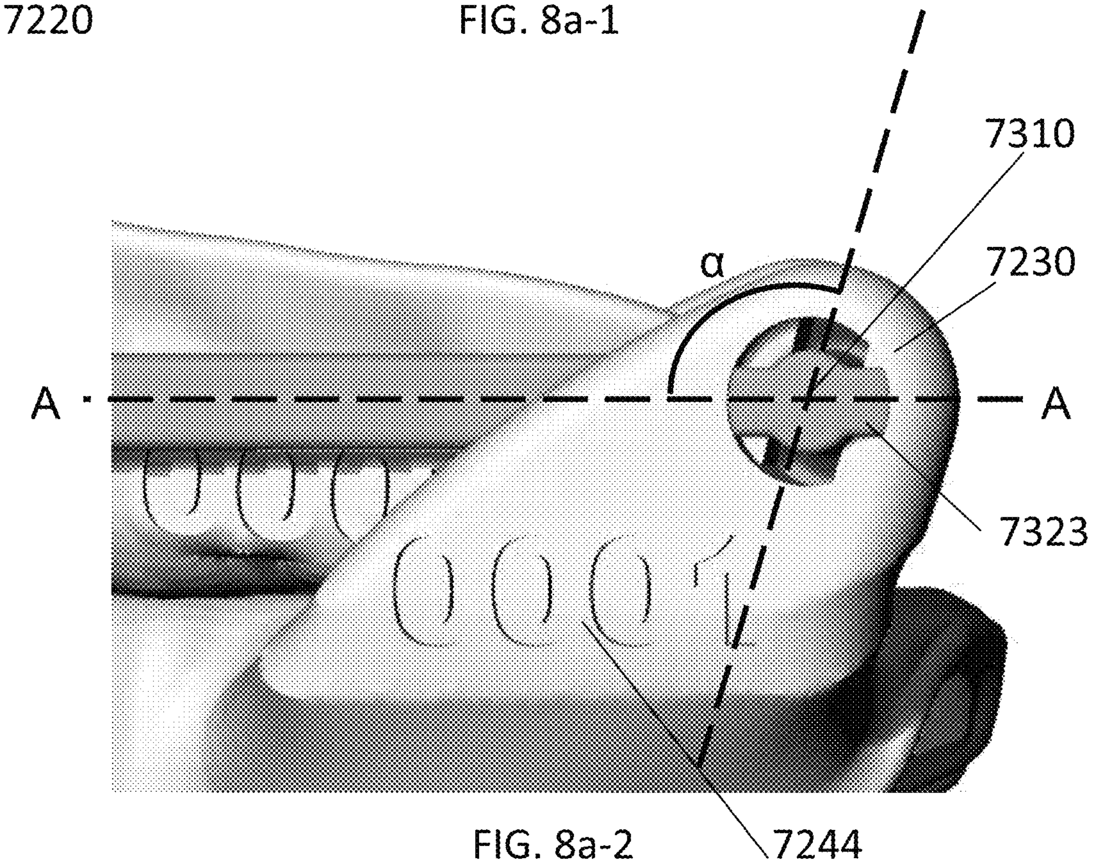
Figure 8B:
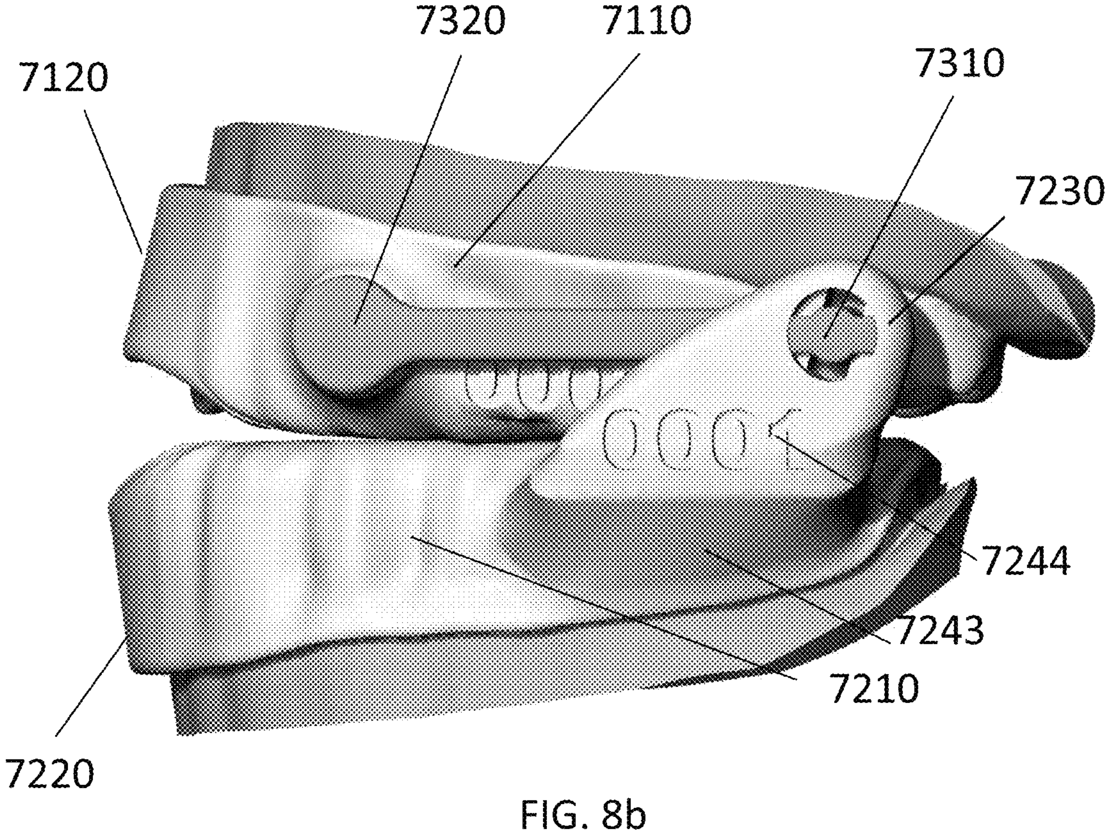
Figure 8C:
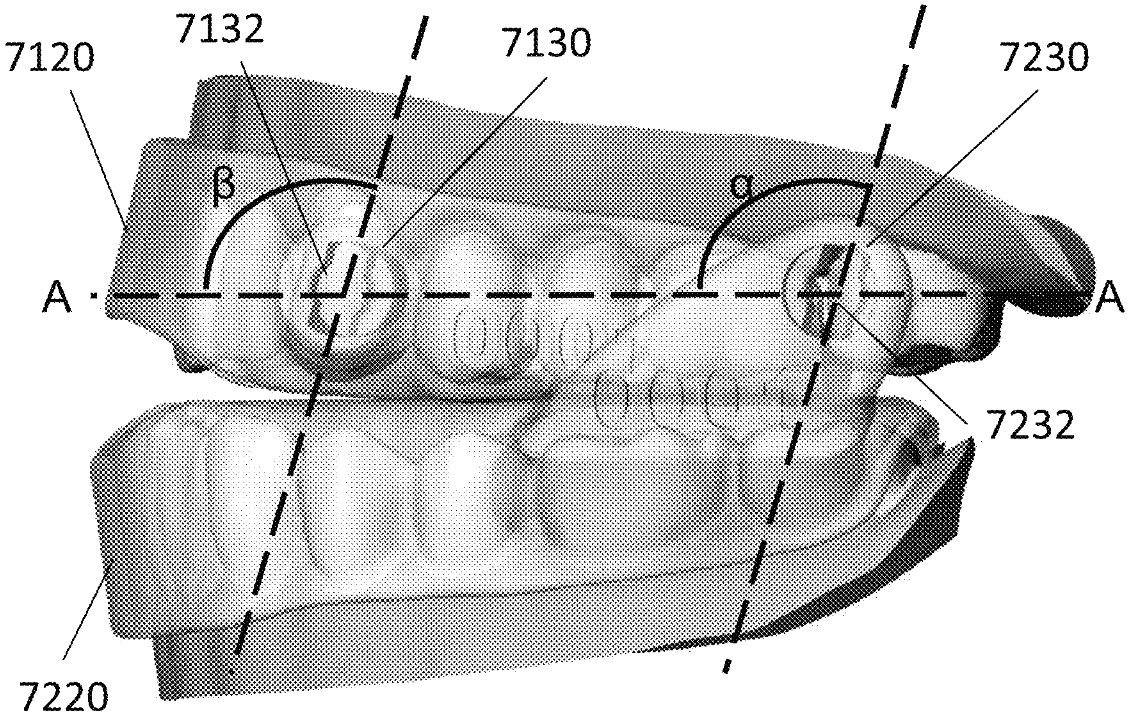
Figure 8D:
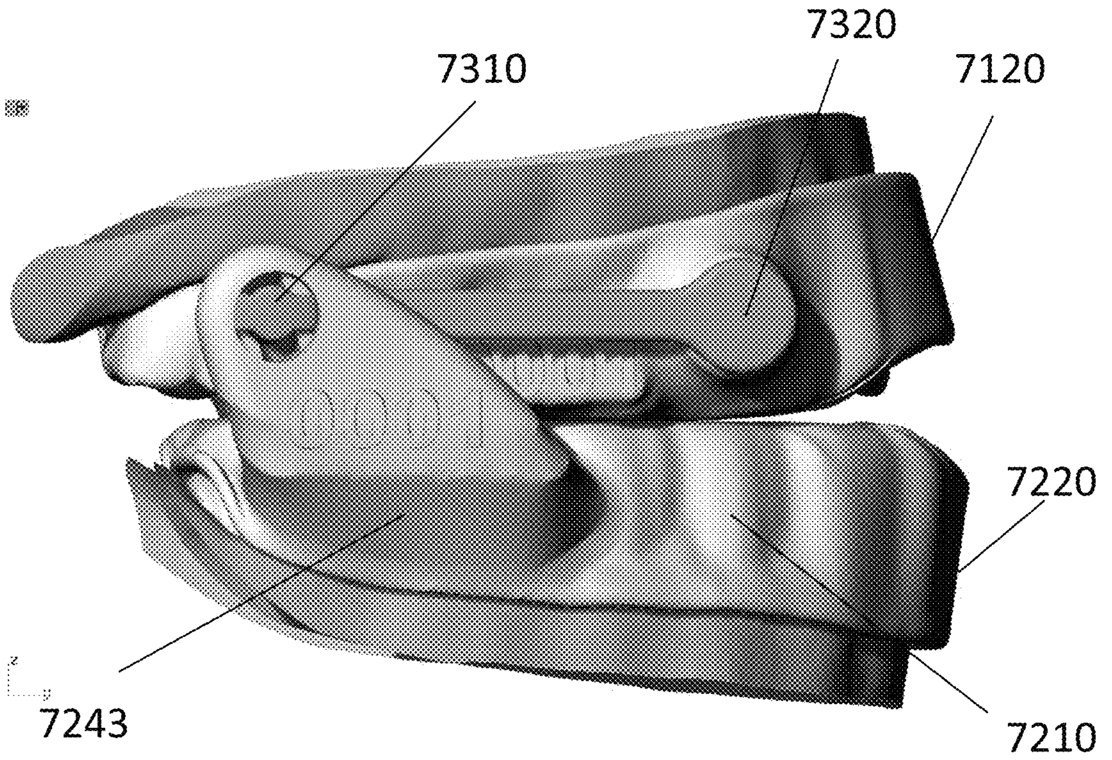
Figure 8E:
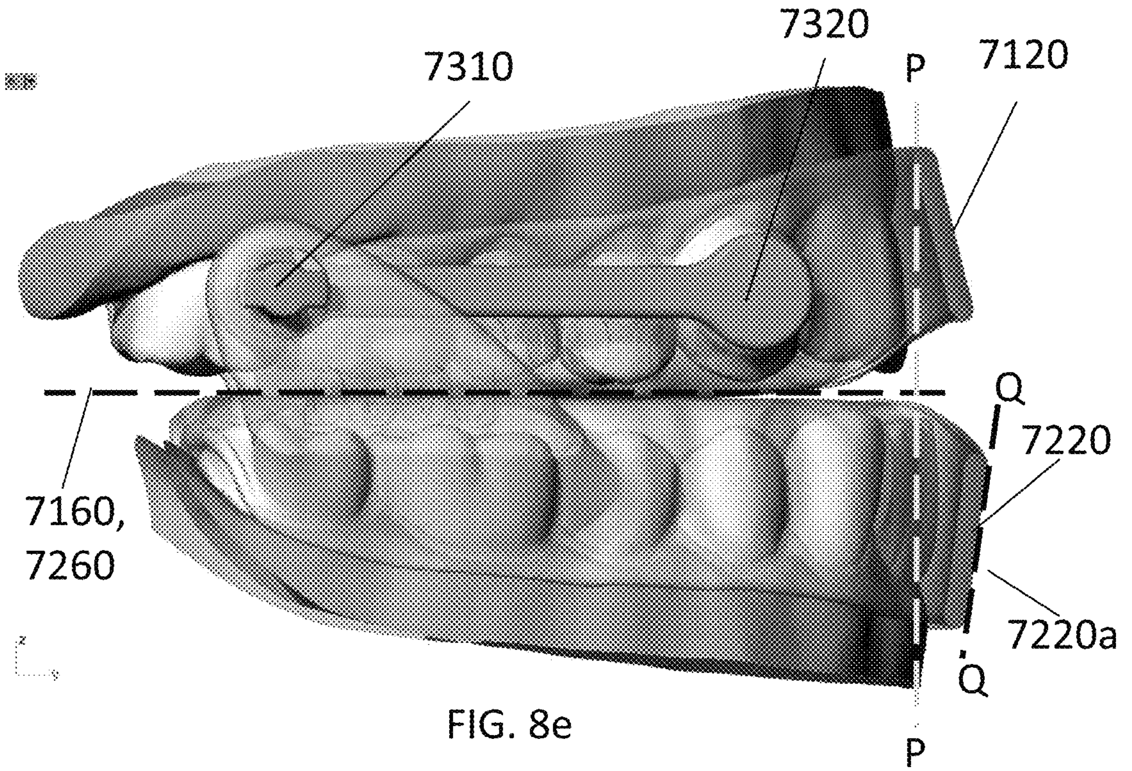

As illustrated in FIGS. 7*a* and 8*e*, the upper splint connection points 7130 are preferably provided in the region of the canines. Preferably, the upper splint connection points 7130 are made as small as possible and may include a rounded shape to prevent irritation within the mouth. Preferably, the shape and size of the contact surface of the upper splint connection point 7130 substantially correspond to the shape and size of the second rod end 7320 (see FIGS. 7*a* to 7*f* and FIGS. 8*a* to 8*e*).

The lower splint 7200, as illustrated in FIGS. 7*a* to 8*e*, includes two mandible or lower gutter portions 7210 designed to fit over at least a portion of one or more teeth on each side of the mandible. The lower gutter portions 7210 may cover a plurality of teeth in the region between the molars and canine on the mandible. A mandible or lower band portion 7220 is preferably provided between the two lower gutter portions 7210 to join the two lower gutter portions 7210 together. The lower band portion 7220 may be designed to extend between the two lower gutter portions 7210 across the front portion of the lateral and central incisors and may not engage with the internal or the external surface of these incisor teeth. Here, the lower band portion 7220 reduces the visual impact of the lower splint 7200 when inserted within the patient's mouth. Preferably, the lower splint 7200 is formed as a single piece with the two lower gutter portions 7210 and the lower band portion 7220 integrally formed together.

However, it is noted that the lower splint 7200 may include a single lower gutter portion 7210 designed to fit over all of the teeth of the mandible respectively, thus no lower band portion 7220 is required in such a lower splint. Such a lower splint may be more intrusive within the mouth. Such a lower splint may be used when the splint is used to treat Bruxism alone or simultaneously with treating obstructive sleep apnea.

As shown in FIGS. 9*a* and 9*b*, the lower band portion 7220 may comprise rounded or smoothed edges, including at least one of the top and bottom edges to reduce or prevent irritation to the teeth or gums on the mandible or maxilla. In one arrangement, the top edge 7222 or bottom edge 7224 or both may have a tear-drop or drop-shape. FIGS. 9*a* and 9*b* depict the lower band portion. However, the upper band portion 7120 may also be configured in the same way as the lower band portion 7220 shown in FIGS. 9*a* and 9*b*, such that it may include rounded or smoothed top edges or bottom edges or both. Alternatively, or additionally, the other outer edges 7118, 7218 (FIGS. 11*b*, 12*a*) of the upper or lower splint, particularly the edges of the gutter portion, may have rounded, smoothed or drop-shaped as further described below.

As particularly seen in FIG. 8*e*, the lower band portion 7220 may be inclined relative to a plane P-P perpendicular to the sliding plane surface 7160, 7260 (which may be referred to as an upper sliding plane surface and a lower sliding plane surface), which is parallel to the occlusal plane. The front surface 7220*a* of the lower band portion 7220 is inclined or angled (line Q-Q in FIG. 8*e*) to follow the angle of the incisors to prevent protrusion of the lower band portion 7220 into the inside of the lips. In other words, the front surface 7220*a* of the lower band portion 7220 angles slightly outwards from the bottom to the top in use thereby forming an acute angle with the lower sliding plane surface. In a similar manner (as seen in FIG. 8*e*) the upper band portion 7120 may also be angled to follow the angle of the patient's incisors (thereby forming an acute angle with the upper sliding plane surface) and may include rounded or smoothed top and bottom edges to reduce irritation of the maxilla gums. Such a design preferably prevents protruding too far inside of the lips. The band of prior art device can be located very far from the teeth in the case of angled incisors. Vestibular bands may be replaced by lingual bands and angles may be adjustable parameters. It is appreciated that the upper band portion 7120 or the lower band portion 7220 as such may be provided with different designs of MADs and the specific arrangement of other components such as the gutter portion design may vary.

As seen in FIGS. 7*a* to 10*b* the lower splint 7200 also may include one or more of lower splint connection points 7230, preferably a pair of points, one on each side of the lower splint 7200. Each lower splint connection point 7230 may be configured to allow connection to a first end 7310 of a respective one of the pair of connecting rods 7300 to the lower splint 7200 (FIGS. 7*c*, 7*d* and 8*b*). The lower splint connection points 7230 may be elevated relative to the lower gutter portions 7210. Preferably, the elevated lower splint connection points 7230 are adjacent the upper gutter portions 7110 on the upper splint 7100 (FIGS. 7*d*, 8*a*-1 to 8*c*). The lower splint connection point 7230 is preferably provided in the area of molars, such as the second molar (FIG. 10*a*). Thus, each one of the pair of connecting rods 7300 may be configured to substantially laterally connect the upper splint 7100 and the lower splint 7200, with the second end 7320 of the connecting rod 7300 connected to the upper splint 7100 and the first end 7310 of the connecting rod 7300 connected to the lower splint 7200 (FIGS. 7, 8). The lower splint connection points 7230 on the lower splint 7200 may be elevated in a position so that when the connecting rods 7300 are connected to the upper splint 7100 and lower splint 7200 the connecting rods 7300 are positioned substantially parallel with the Frankfort plane. In such an arrangement the traction force of the connecting rods 7300 is substantially parallel to the occlusal plane, which reduces the likelihood of the intra-oral device or MAD coming loose in use. This arrangement of the connecting rods 7300 is also advantageous for retaining the mandible in an advanced position.

As particularly illustrated in FIGS. 10*a* to 10*c*, each of the lower splint connection points 7230 may be formed in a wing structure 7240 that protrudes laterally from the lower splint 7200. The wing structure 7240 may have a curved structure to assist in supporting a patient's mucosa of the cheek when the intra-oral device or MAD is inserted in the patient's mouth. The wing structure 7240 may comprise a curved structure or filled portion 7243 connecting the substantially laterally extending wing base 7242 to the respective portion of the lower gutter portion (FIG. 10*c*). The filled portion 7243 is preferably contoured to provide support to the cheek so as to avoid dead space between the wing structure 7240/lower gutter portion 7220 and the mucosa of the cheek. The filled portion 7243 may extend from an outer side 7244 of the wing structure 7240 until the outer edge 7218 of the respective gutter portion in a substantially flat or even a slightly convex fashion, preferably without a concave portion.

Prior art devices meet the gutter wall in a side wall portion located in the middle of the gutter side wall. This transition area at the middle side wall portion overall has a concave shape.

Preferably, the wing structure 7240 is contoured to avoid edges or curvatures with small radii in order to avoid causing discomfort. Preferably, the length of the wing base 7242 and of the filled portion 7243 parallel to the direction of extension of the mandibular is selected so as to avoid edges, curvatures with small radii and/or dead space between the wing structure 7240/lower gutter portion and the mucosa of the check thereby increasing comfort. In other words, the wing structure may be less angular and the merging with the gutter may be optimized. The extremities of the wing structure may be slightly curved.

Prior art devices comprise connection portions having a shape designed to be able to withstand the applied force with the lowest material consumption possible, particularly since the material consumption increases the material costs and production time. Compared to prior art devices, wing base 7242 and filled portion 7243 are longer than those prior art devices in order to avoid discomfort.

It is appreciated that the above wing structure and particularly the filled portion may also be provided with different designs of MADs and the specific arrangement of other components, such as the gutter or band portion design, may vary.

The wing structure may comprise an elevated portion 7245 elevating from the wing base 7242 (FIGS. 10*a* to 10*c*). Preferably, the lower splint connection point 7230 is located in the elevated portion 7245. The elevated portion 7245 may have a triangular configuration, although other shapes may be used. The lower splint connection point 7230 may be counter sunk within the wing structure 7240 to reduce irritation of a first attachment or rod pin 7312 of the connecting rod 7300 in a patient's mouth when the connecting rod 7300 is attached through the first slot 7232 (FIG. 10*a*) of the lower splint connection point 7230 of the lower splint 7200 and the MAD is in a patient's mouth (FIG. 7). Here, the thickness of the elevated portion 7245 is adapted to accommodate a first rod pin 7312 so that the outer side or surface 7244 of wing structure 7240 is substantial plane. This means that preferably no portion or only a minor portion of the first rod pin 7312 protrudes from the outer side or surface 7244. The first and second rod pins 7312, 7322 may each comprise at least one pin protrusion 7313, 7323 extending laterally from the upper end of the rod pin (FIG. 10*f*). The lower splint connection point 7230 may comprise a recessed portion adapted to accommodate the at least one first pin protrusion 7313 (FIG. 10*a*). Preferably, the recessed portion is adapted to accommodate rotation of the at least one first pin protrusion 7313. The lower splint connection point 7230 may have a through hole with a shape adapted to the shape of the first attachment or rod pin 7312. The outer side 7244 may be arranged substantially parallel to an inner side. The inner side may be arranged as a substantially flat surface, preferably in an angle of (about) 90° to the wing base 7242 or the occlusal or sliding plane surface 7160, 7260 (FIG. 10*c*). This may improve the fixation of the connecting rod. The lower splint connection points 7230 of the lower splint 7200 may be formed as first slots 7232 configured to receive the first rod pins 7312 of the connecting rods 7300 (see FIG. 10*a*).

It is appreciated that the counter sunk connection point as well as the inner and outer surface may also be provided with different designs of MADs and the specific arrangement of other components, such as the particular wing structure arrangement in general, may vary.

The upper splint connection point(s) 7130 of the upper splint 7100 may be formed as second slot(s) 7132 configured to receive the second rod pin(s) 7322 of the connecting rod(s) (FIGS. 7, 8). Preferably, the first slots 7232 and the second slots 7132 have complementary shapes to the shapes of the first rod pins 7312 and second rod pins 7322 respectively to facilitate insertion of the first rod pins 7312 and second rod pins 7322 into the first slots 7232 and the second slots 7132, respectively. The first slots 7232 and second slots 7132 are configured to allow the connecting rods 7300 to pivot or swivel within the slots 7132, 7232 in use to enable the opening and closing movement of the mandible in use.

It is appreciated that the above described connection of the rod to the lower splint(s) may also be provided with different designs of MADs and the specific arrangement of other components, such as the gutter or band portion design, may vary.

The assembly and disassembly of the connecting rods 7300 to the upper splint 7100 and lower splint 7200 will now be described in relation to the lower splint using the first slot 7232, the first rod pin 7312 and the lower connection point 7230. However, it is to be understood that the same process is used to assemble and disassemble the upper splint and the connecting rods using the second slot 7132, the second rod pin 7322 and the upper connection point 7130. For assembly the first rod pins 7312 may be inserted into and through the first slot 7232 in the lower connecting point 7230 by aligning the first rod pins 7312 with the first slots 7232. Once inserted the connecting rod 7300 is rotated or pivoted around in the first slot 7232 to prevent the first rod pins 7312 from releasing out of the slot. For disassembly of the connecting rods 7300 from the first slot 7232 the connecting rod 7300 is preferably rotated or pivoted to realign the first rod pins 7312 with the first slots 7232 to allow removal of the rod pins through the slot.

To avoid detachment of the connecting rods 7300 during use or for detachment for cleaning the angle α, β of the first and second slot(s) 7132, 7232 are preferably set relative to the axis of the connecting rod 7300 to ensure that there is an at least one quarter turn in order to disassemble the connecting rod 7300. For instance, an at least one quarter turn in the clockwise direction is to be ensured in FIG. 8*c*. The longitudinal axis of the first slot 7232 and the longitudinal axis of the connecting rod 7300 in use (i.e. application by the user with closed mouth) may be arranged in a first obtuse angle α. Preferably the angle α is in a range of 90° to 170°, more preferably of 100° to 160 or of 110° or 130° to 150°, and most preferably of 105° to 135° (FIG. 8*c*).

Preferably, the longitudinal axis of the second slot 7132 and the longitudinal axis of the connecting rod 7300 in use (i.e. application by the user with closed mouth) are arranged in a second obtuse angle (β). Preferably, the second obtuse angle (β) is in a range of 90° to 170°, more preferably of 100° to 160°, or of 110° or 130° to 150° and most preferably of 105° to 135° (FIG. 8*c*). The angles α and β may have the same value. Moreover, angle α and/or β may preferably be 105°. An angle of the longitudinal axis of the first slot 7232 to the sliding plane surface 7260 or occlusal plane may be adjustable. Similarly, the angle of the longitudinal axis of the second slot 7132 to the sliding plane surface 7160 may also be adjustable. The angle may be adjusted considering the relative orientation of the connecting rod 7300 to the sliding plane surface 7160, 7260 or occlusal plane. With such a tailored design parameter, the risk of an unintended disassembly can be further reduced.

It is appreciated that the above described angular relationship between the longitudinal axis of the slots to the longitudinal axis of the connecting rod in use may also be provided with different designs of MADs and the specific arrangement of other components, such as the gutter or band portion design or the general wing design, may vary.

Optionally, a flow sensor, pressure sensor, radio frequency identification (RFID) sensor or any other type of sensor may be incorporated into the MAD, preferably in the lower splint, most preferably into the wing structure 7240. The sensor arrangement may be the sensor arrangement as disclosed in the patent document EP 2575706. The compliance monitoring system and its sensors disclosed in EP 2575706 are part of the described technology and are incorporated here in its entirety by reference.

The outer side 7244 of the wing structure 7240 may also provide a surface for insertion or engraving of a label such as an identification label, brand, trademark, name, number, code or similar such label. Alternatively, or additionally, the label might be engraved in the substantially flat upper or lower band portion or on any other visible and purposely flat/even designed portion such as a portion in the gutter region of the upper splint (FIG. 8). Engraving the label on the substantially flat portion, and particularly in a portion of the wing structure not interfering with the lower connecting point 7230, increases the readability of the label. This particularly applies in comparison with MADs having labels on thin and uneven gutter walls.

It is appreciated that the engraving of a label may also be provided with different designs of MADs and the specific arrangement of other components, such as the gutter or band portion design, may vary as long as the outer side of a wing structure is substantially flat.

The degree of advancement of the mandible may be defined by the length of the connecting rods 7300. The connecting rods 7300 may be formed in a range of lengths for example in lengths from 20 mm to 40 mm, such as 21 mm to 36 mm, with incrementing sizes for example of 0.5 mm, 1 mm or 1.5 mm. The connecting rods 7300 may be manually attachable to and detachable from the splints 7100, 7200 to allow interchanging of the connecting rods 7300 for different lengths to adjust the level of mandible advancement. Alternatively the length of the connecting rods 7300 may be adjustable to facilitate adjustments in the level of mandible advancement as described in the U.S. Pat. No. 7,146,982 the contents of which is incorporated herein in its entirety.

As shown in FIG. 10*f*, each of the connecting rods 7300 may be removable and replaceable and may include the first rod pin 7312 at the first end 7310, for connection to the lower splint connection point 7230 on the lower splint 7200, and a second rod pin 7322 at the second end 7320 for connection to the upper splint connection point 7130 on the upper splint 7100. In the application position, the first attachment or rod pin 7312 may be located and may protrude from an outer side of the connecting rod 7300 and the second rod pin 7322 may be located and may protrude from an opposing inner side of the connecting rod 7300. In this arrangement, each of the connecting rods 7300 may be positioned between the upper splint 7100 and the lower splint 7200, preferably between the upper splint 7100 and the elevated splint connection point 7230 of the wing structure 7240. This also minimizes contact of the connecting rods 7300 with the mucosa of the cheek in the patient's mouth in use.

FIGS. 11*a*, 11*b* and 12*a*-12*c* show, inter alia, the retention profile of at least one of the upper and lower gutter portions 7110, 7210. The gripping or clipping features of the lower gutter portion 7210 will now be described with reference to FIGS. 11*a*, 11*b*, 12*a-c*. However, it is acknowledge that the same or similar features as those described below may be applied to the at least one upper gutter portion as seen in FIG. 12*d*. Moreover, the discussion is focussed on one gutter portion. It is appreciated that the described technology also applies to a plurality of upper or lower gutter portions such as two upper (i.e. left and right upper gutter portion) and two lower (i.e. left and right lower gutter portion) gutter portions.

FIG. 11*b* shows a cross section of the mandible gutter portion. The thicker inner line having generally the same shape as the respective tooth, on which portion of the lower gutter portion is inserted, represents the retention portion 7261. An equivalent retention portion 7161 may be present in the upper gutter portion (see FIG. 12*d*). The retention portion may also be named retention area. The profile of this retention portion 7261 is the retention profile. As can be seen in FIGS. 11*b*, 12*a-b*, at least a portion of the area over the arch of the crown of the teeth 7216 may form the retention portion 7261 that is responsible for retaining the lower splint 7200 on the teeth. In the embodiment of FIG. 11*b*, almost the whole area over the arch of the crown 7216 of the teeth (not shown) is a retention portion 7261. Preferably, the retention portion 7261 is located in a side portion of the crown region, most preferably on both side portions of a crown region of a tooth.

In some forms, a thickness of the retention profile varies across the entire retention portion. The retention profile in the retention portion 7261 of the lower gutter portions 7210 has a varying thickness EP over the respective tooth (FIGS. 11*b*, 12*a-c*). When it is referred to the profile of the gutter or to the retention profile, a profile in the cross section is to be understood to mean in a plane perpendicular to the extension of the gutter portion or mandible or maxilla, as shown in FIG. 11*b*. The varying thickness of the at least one upper gutter portion or the at least one lower gutter portion across the profile of the teeth is to be understood as a thickness variance in the same cross section in a plane perpendicular to the extension of the gutter portion or mandible or maxilla (FIGS. 11*a*, 11*b*, 12*a* to 12*d*).

In particular as seen in FIG. 11*b* and FIGS. 12*a* and 12*d*, the area over the tips of the cusp of the teeth may have a reduced first cusp thickness EPc1 compared the second thickness Epc2 of an area between the cusp tips of the teeth. This provides the lower gutter portions 7210, 7110 with increased elasticity or softness to improve gripping or retention on the teeth. In particular, a further reduced first cusp thickness Epc1 may allow an easier movement of at least one of the first inner side wall portion 7162, 7262 and the second inner side wall portion 7166, 7266 relative to the tooth. On the other hand, further reducing the first cusp thickness Epc1 may negatively influence the wear resistance, particularly in the case of bruxism.

The thickness of the first cusp thickness and the average thickness of the portion forming the below discussed sliding plane surface, preferably on each upper and lower gutter, may be in the range of 0.2 mm to 12 mm, preferably 3 mm to 10 mm, more preferably in the range of 4 to 7 mm and most preferably about 5 mm.

Sliding plane surface 7260 of the lower gutter portion 7210 (FIGS. 11*a*, 11*b* and 12*a*) and sliding plane surface 7160 of the upper gutter portion 7110 (FIG. 12*d*) are, in use, in contact with each other. The sliding plane surfaces 7260, 7160 may be substantially flat and parallel to the occlusal plane. Sliding plane surfaces 7260, 7160 may extend along a major part or the entire width of the underlying teeth (FIG. 12*a*, 12*d*). The sliding plane surface 7260 of the lower gutter portion 7210 preferably joins a first inner side wall portion 7262 of the gutter portion 7210 in a joining section 7264 having a first joining thickness EPj. The first inner side wall portion 7262 may extend from the first joining section 7264 generally along the side wall b or coronary part of the tooth to the apex a or larger contour line a' of the tooth's side wall b. A similar arrangement of the sliding plane 7160, a first inner side wall portion 7162, a joining section 7164 and a first joining thickness EPj are seen on the upper gutter portion 7110 (see FIG. 12*d*).

The apex a of the tooth is to be understood as the outermost part or the larger contour line a' of the respective tooth seen in the insertion direction I. Apex a shown in cross-sectional view of FIGS. 12*a* and 12*d* may be equivalent to the larger contour line a' extending around the tooth (dash-dotted line in FIGS. 12*a*, 12*c*, 12*d*) and representing the outermost portions of the side wall b of the tooth. The insertion direction I is the direction, in which the lower gutter portion 7210 or the upper gutter portion 7110 is put on the respective tooth. As in the embodiment of FIGS. 12*a* and 12*d*, the insertion direction I may be parallel to a longitudinal axis of the respective tooth contact with the lower gutter portion 7210 or the upper gutter portion 7110 respectively. The apex a or the larger contour line a' is then the outermost portion of the respective tooth in relation to the longitudinal axis of the tooth. If the insertion direction is inclined in relation to the longitudinal axis of the respective tooth, the apex a to be located at the outermost portion seen from the insertion direction I may be at a different location. The outermost portion seen from the insertion direction I considered as being the apex a could alternatively be defined as the portions of the respective tooth defining the edges or outline of a projection surface of a projection projected from the insertion direction I. The location of the apex a depends on the insertion direction I, the height and the shape of the respective tooth (FIG. 12*c*).

A second portion 7266, 7166 of the inner side wall of the lower or upper gutter portion may extend from the apex a or the larger contour line a' preferably in the direction of the gingival part of the tooth. Preferably, the shape of the second portion 7266, 7166 of the inner side wall is an undercut portion 7266, 7166. The undercut portion of the portion of the teeth is a radially outermost point of the portion of the teeth with respect to a longitudinal axis extending substantially perpendicular to a gingival part of the portion of the teeth. The undercut portion 7266, 7166 extending from apex a has a shape that corresponds to the shape of the adjacent portion of the tooth and is adapted to contact a sidewall of the portion of the tooth. The undercut portion 7266, 7166 of the retention profile is adapted to contact the apex a of the sidewall of the portion of the tooth. Accordingly, the shape of the undercut portion 7266, 7166 of the inner wall of the gutter may extend from apex a in an inward direction towards the gingival part of the tooth. The undercut portion or the second portion 7266, 7166 may intersect with an inner receiving portion 7268, 7168 at a second joining section 7269. The thickness EPj at the joining section 7264 is preferably increased compared to the thickness EPa in or near the area of the apex a or the larger contour line a'. The thickness EPa is adapted to contact the an apex a of a sidewall of a tooth. The thickness of the side wall in or near the apex a may be reduced compared to at least one of the thickness EP of the side wall in the second joining section 7269, 7169 or the thickness in the inner receiving portion 7268, 7168. The thickness EP may gradually decrease from the first joining section 7264, 7164 towards the apex a and may increase again towards the second joining section 7269, 7169. Therefore, the thickness EPa in or near the area of the apex a is less than the first cusp thickness EPc1, which is the thickness EPj at the joining section 7264. The undercut thickness at the undercut portion 7266, 7166 of the retention profile is less than the first cusp thickness EPc1. The thickness EPa may be an apex thickness that is a minimum thickness, which is adapted to contact the apex a of a sidewall of the portion of the teeth. Preferably, at least a portion of the side wall of the gutter portion is adapted to elastically clip on at least one tooth and the undercut portion(s) may hold the device on the tooth.

The inner receiving portion 7268 is oriented so that a minimum distance to the tooth or gum is maintained, thereby avoiding damages or irritation of the gum during insertion or use. Preferably, also the second joining section 7269, 7169 is located such that a certain vertical and lateral minimum distance is maintained further reducing the risk of irritation. Preferably, the inner receiving portion 7268, 7168 is adapted to receive a tooth upon insertion of the intra-oral device or MAD into the mouth.

A gutter portion preferably comprises at lateral sides above described first inner side wall portion 7262, 7162, second inner side wall portion/undercut portion 7266, 7166, first joining section 7264, 7164, inner receiving portion 7268, 7168 and second joining section 7269, 7169. Preferably, the lower and upper gutter portions 7210, 7110 each comprise two receiving portions 7268, 7168 adapted to elastically spread apart the side walls of the gutter portion during insertion of the tooth in the gutter portion. The inner receiving portions 7268, 7168 may angle outwardly and thus, in use, away from the gingival part. The inner receiving portions 7268, 7168 may be angled outwardly from the gingival part so that each inner receiving portion 7268, 7168 and a free end of the retention profile avoid contact with the gingival part.

The undercut portion 7266, 7166 may define an undercut u. The undercut may be understood to be the distance between a tangential plane T-T in which the apex a or the larger contour line a' is located to the thereto parallel plane B-B in which the second joining section 7269 is located (FIG. 12*b*, 12*c*). If the intra-oral or MAD comprises flexible gutter side wall portions an increased undercut u and thus an increased retention may be designed. The undercut portion 7266, 7166 is a retention surface predominantly creating the retention force avoiding removal of the gutter. The undercut portion 7266, 7166 and, thus, the undercut u, may be balanced so that the undercut ul on a left side of a lower gutter portion 7210 substantially corresponds to the undercut ur on a right side of the same lower gutter portion 7210. Alternatively, or additionally, the overall undercut, preferably the retention surface or retention force below the apex a of a lower splint 7200 may also be balanced so that the undercut u of a left lower gutter portion 72101 substantially corresponds to the undercut u of a lower right gutter portion 7210*r*. With an increasing retention surface of the undercut portion 7266, i.e. an increasing surface creating the retention force below the apex a or larger contour line a', also the overall retention surface 7261 increases (FIG. 12*c*) since the undercut portion is a part of the retention portion 7261. The undercut portion 7266 may be located on all accessible areas below the larger contour line a' extending around the tooth, e.g. the left and right side of the same lower gutter portion 7210 covering the left and right side wall b of the tooth. If the gap(s) between adjacent teeth allow(s), or if such an adjacent tooth is missing, also the side walls of the tooth connecting the left and right side walls b of the tooth may be used. Accordingly, an increasing undercut portion 7266, 7166 also increases the gripping surface of the retention portion. Therefore, the surface pressure applied to a unit area in the respective portions of the respective tooth engaging with the lower gutter portion may be reduced. The surface of the undercut portion of one tooth is preferably chosen to be in the range of 15 $mm^2$ to 60 $mm^2$, more preferably to 30 $mm^2$ to 40 $mm^2$, and most preferably to 33 $mm^2$. The retention surface, preferably of the undercut portion 7266, 7166, may be selected such that the retention force is in the range of 0 N and 100 N, more preferably in the range of 10 N to 50 N, and most preferably in about 20 N. This retention force is preferably of one side of a gutter, left or right. It is appreciated that the above described profile, in particular the (different) thickness variation(s) of the profile, the undercut, the retention surface, the retention force and undercut portion may also be provided with different designs of MADs and the specific arrangement of other components, such as parts not belonging to a gutter portion, may vary. Preferably, the value of the undercut, particularly for the maximum retention may vary in a range of 0 to 1 mm Preferably, the value of the undercut is about 0 mm at the larger contour line a'. Also preferably, it is about 1 mm, preferably being the maximum value at or defining the limit of the zone 7266, 7166, preferably being the depth of the undercut u (see FIG. 12*c*). In practice, the value of the undercut may vary depending on the shape of the teeth. For example, on flat teeth an undercut of 1 mm might not be realizable.

The lower outer edge 7218 of the lower gutter portion 7210 as well as the upper outer edge 7118 of the upper gutter portion 7110 may be configured to be positioned adjacent to a patient's gums and may also include a rounded profile to improve comfort in use. Preferably, the radius of the outer edge(s) may be provided with an adjustable radius. For instance, the radius may be different in different portions of the upper or lower gutter portions 7110, 7210. The radius may also be tailored to the overall configuration of the sectional profile of the gutter portion, which may be adapted according to the patient's anatomy. As outlined above, although the gutter portion is predominantly described with reference to a lower gutter portion 7210, the same technology and considerations may be applied to at least one upper gutter portion 7110, which is also part of the disclosed technology of this application and shown in FIG. 12*d*.

At least a portion of the intra-oral device or MAD is preferably made of a powder material, most preferably suitable for 3D printing, e.g. selective laser sintering but can be produced by any other suitable manufacturing technology, e.g. a milling technology. The material may be a biocompatible material, and may be sufficiently rigid for the constraints. Preferably, a polymer material is used, most preferably polyamide is used. It is thus possible to efficiently and effectively produce an intraoral appliance that is preferably light and also comfortable to wear. The patients therefore do actually use the appliance more frequently leading to better treatment results. Moreover, the manufacturing time, labour costs as well as the material costs may be substantially reduced. For a better clipping, an elastically deformable material is preferred.

The intra-oral or MAD is formed using a computer aided design (CAD) and computer aided manufacturing (CAM) process. In such a process an electronic image of patient's teeth is prepared and used to design the MAD to ensure that the MAD comfortably fits the patient's teeth. The electronic image of the patient's teeth may be produced from a scan of the patient's mouth or based on a scan of a mould of the patient's teeth. A mould of the patient's teeth may be prepared based on an impression of the patient's teeth that is taken, for example by a dentist or dental technician.

The use of CAD to design a patient's MAD provides for a customised product that is specifically designed to fit the patient's mouth. This provides increased comfort for the patient when wearing the MAD. The upper gutter portions 7110 and the lower gutter portions 7210 are shaped to closely match the contours of the patient's teeth to provide an improved fit, retention over the teeth and comfort, whilst minimising damages to the teeth and irritations to the soft tissues of the gums.

In the present technology the retention of the intra-oral device or MAD 7000 in the mouth may be further improved by determining an optimum area of retention for the lower gutter portions 7110 and the upper gutter portions 7110 to grip the teeth. FIG. 13 illustrates an exemplary process 7500 of designing a MAD including an optimised retention profile. The process may include the step 7510 of obtaining an electronic image of the patient's dental arch including some or all of the teeth. This may be performed by uploading (or downloading) a scan file of the patient's teeth. The scan itself may be performed at a remote location, such as a dentist office, and sent for processing by way of any storage medium, such as a portable hard-drive, a memory stick, a recorded DVD etc., or transmitted via the internet. Alternatively, the file may be obtained by a scanning device directly connected to the computer. Then in step 7520, the computer processor preferably determines a retention area of the available teeth for gripping, based on the obtained electronic image. In particular, the processor assesses the area available around at least a portion of the outer arch of the crown of the patient's particular teeth and calculates what sections of the crown of the teeth are available for gripping or retention. In step 7530 the processor calculates a retention profile that matches the patient's teeth. Then in step 7540 the processor designs the lower gutter portions 7210 and the upper gutter portions 7110 to include the calculated retention profile. The computerised design based on optimised estimate of the gripping are of the teeth in the proposed intra-oral or MAD 7000 has increased retention while applying less pressure on the user's teeth. The potential for formation of pressure points or areas, where the gutter portion grips the tooth particularly strongly, causing potential damage to the tooth, is minimised. Furthermore, this arrangement also prevents any movement of the teeth caused by the use of the intra-oral device or MAD.

An undercut portion 7266, 7166 may be determined considering the apex a of the sidewall b of the portion of the teeth and considering a minimum distance to the gingival part of the portion of the teeth. Preferably, the consideration of the apex a includes the consideration of the direction of insertion I of the portion of the teeth into the respective gutter portion as well as the shape and height of the inserted portion of the teeth. The thickness EP of the profile is preferably calculated considering the determined undercut portion and considering the required elasticity of at least a portion of the gutter side walls so that the walls are adapted to clip on at least a portion of the teeth. The end or inner receiving portion 7268, 7168 of the profile may be located in the application position adjacent to the gingival part. The end or inner receiving portion may be arranged at a minimum distance to the gingival part, particularly to protect it from contact or injury.

The method may further comprise the step of manufacturing the intra-oral device or mandibular advancement device according to the calculated design. The intra-oral device may be manufactured using a computer aided manufacturing technique, for instance a rapid prototyping or 3D printing technology such as selective laser sintering. The selective laser sintering may comprise the layer-wise sintering of a powder material.

The intra-oral device described including a lower splint 7200 with the wing structure 7240 and an upper splint 7100 that are coupled together via the rods 7300 may be used to treat Bruxism. In such a device at least one of the upper or lower splints preferably cover all or most of the teeth on the maxilla or mandible respectively. Preferably the rods 7300 are attached such that it does not provide an opened mouth. The rods are still used to attach the upper and lower splints but are set at no or 0 mm protrusion if only treating bruxism. Alternatively, the splints only may be used, i.e., no wing structure 7240 or connecting rods 7300 are provided and the splints are simply retained on the teeth and are not connected to each other. Preferably at least one of the upper or lower splints 7100, 7200 cover all or most of the teeth on the maxilla or mandible respectively.

In some arrangements a device may be combined to treat both sleep disordered breathing (e.g. snoring, hypopneas, or Apneas) and Bruxism at the same time.

It should be noted that in the above description, any reference made to various steps does not imply that the respective functions have to be performed in a specific order and that at least some of these functions may be performed in a different order or simultaneously.

Glossary

In certain forms of the present technology, one or more of the following definitions may apply. In other forms of the present technology, alternative definitions may apply.

1.6.1 General

1.6.2 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. In one form in adults, the following either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed.

1.6.3 Anatomy of the Skull

Frankfort plane: A plane passing through the right and left portion and the left orbitale. Also called Frankfort horizontal plane.

Frontal bone: The frontal bone includes a large vertical portion, the *Squama frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the *Squama occipitalis*.

Occlusal plane: a plane passing through the occlusal or biting surfaces of the teeth. It represents the mean of the curvature of the occlusal surface.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

1.6.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

1.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms “a”, “an”, and “the” include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms “comprises” and “comprising” should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms “first” and “second” may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

The proposed technology also covers all further features shown in the figures individually although they may not have been described in the afore description. The present technology covers further embodiments with any combination of features from different embodiments described above. Reference signs in the claims are provided merely as a clarifying example and shall not be construed as limiting the scope of the claims in any way.

The present technology also covers and relates to the exact terms, features, values and ranges etc. in case these terms, features, values and ranges etc. are used in conjunction with terms such as about, around, generally, substantially, essentially, at least etc. (i.e., “about 3” shall also cover exactly 3 or “essentially radial” or “or “substantially radial” shall also include a reference to “radial”).

REFERENCE SIGNS LIST

| Item | Reference Number |
|---|---|
| Intra-oral or mandibular advancement device (MAD) | 7000 |
| upper splint | 7100 |
| maxilla/upper gutter portion | 7110 |
| outer edge mandible gutter portion | 7118 |
| maxilla/upper band portion | 7120 |
| upper splint connection point | 7130 |
| second slot | 7132 |
| second obtuse angle | β |
| lower splint | 7200 |
| mandibular/lower gutter portion | 7210 |
| first attachment/rod pin | 7212 |
| arch of the crown of the teeth | 7216 |
| outer edge mandible gutter portion | 7218 |
| mandibular/lower band portion | 7220 |
| front surface | 7220a |
| top edge | 7222 |
| bottom edge | 7224 |
| lower splint connection point | 7230 |
| first slot | 7232 |
| wing structure | 7240 |
| wing base | 7242 |
| filled portion | 7243 |
| outer side or surface | 7244 |

-continued

| Item | Reference Number |
|---|---|
| elevated portion | 7245 |
| first obtuse angle | α |
| first cusp thickness | EPc1 |
| second thickness between the cusp | EPc2 |
| sliding plane surface | 7160, 7260 |
| retention portion/retention area | 7161, 7261 |
| first inner side wall portion | 7162, 7262 |
| second inner side wall portion/undercut portion | 7166, 7266 |
| first joining section | 7164, 7264 |
| inner receiving portion | 7168, 7268 |
| second joining section | 7169, 7269 |
| connecting rod | 7300 |
| first rod end | 7310 |
| first rod pin | 7312 |
| first pin protrusion | 7313 |
| second rod end | 7320 |
| second rod pin | 7322 |
| second pin protrusion | 7323 |
| process | 7500 |
| obtaining image step | 7510 |
| retention area step | 7520 |
| retention profile step | 7530 |
| Design MAD step | 7540 |
| apex of the side wall of the tooth | a |
| larger contour line of the tooth | a' |
| side wall of the tooth | b |

What is claimed is:

1. An intra-oral device designed to fit in a patient's mouth, comprising:

an upper splint, configured to engage with at least a portion of one or more teeth on the patient's maxilla, wherein the upper splint includes at least one upper gutter portion configured to engage said at least the portion of one or more teeth on the maxilla to retain the upper splint on the patient's maxilla; and a lower splint configured to engage with at least a portion of one or more teeth on the patient's mandible, wherein the lower splint includes at least one lower gutter portion configured to engage said at least the portion of one or more teeth on the mandible to retain the lower splint on the patient's mandible, wherein a thickness of the at least one upper gutter portion and/or the at least one lower gutter portion varies, and a retention portion of the at least one upper gutter portion and/or a retention portion of the at least one lower gutter portion has a varied thickness profile, wherein the upper splint comprises an upper band portion between two upper gutter portions of said at least one upper gutter portion and the upper band portion is configured to extend across a front portion of upper central incisor teeth, wherein the lower splint comprises a lower band portion between two lower gutter portions of said at least one lower gutter portion and the lower band portion is configured to extend across a front portion of lower central incisor teeth while the two lower gutter portions are configured to engage said at least the portion of one or more teeth on the mandible, and wherein the lower band portion is configured to be positioned directly in front of the front portion of the lower central incisor teeth when the intra-oral device is worn by the patient, wherein a surface of the lower band portion is configured to be inclined relative to a first plane that is perpendicular to a lower sliding plane surface when the intra-oral device is worn by the patient, the lower sliding plane surface being configured to be parallel to the patient's occlusal plane, wherein the surface of the lower band portion is configured to angle outwardly from a bottom to a top of the lower band portion to form an acute angle with the lower sliding plane surface when the intra-oral device is worn by the patient, and wherein the surface of the lower band portion forming the acute angle is configured to be positioned in front of the lower central incisor teeth when the intra-oral device is worn by the patient.

2. The intra-oral device according to claim 1, further comprising a pair of connecting rods, each connecting rod having a first rod end configured to connect to the lower splint and a second rod end configured to connect to the upper splint, wherein the pair of connecting rods are configured to maintain the mandible in a set position relative to the maxilla, wherein the set position includes a neutral position or an advanced position relative to the maxilla.

3. The intra-oral device according to claim 1, wherein the at least one upper gutter portion is profiled to match a contour of the portion of one or more teeth on the maxilla to improve retention of the upper splint and/or the at least one lower gutter portion is profiled to match a contour of the portion of one or more teeth on the mandible to improve retention of the lower splint.

4. The intra-oral device according to claim 1, wherein the retention portion of the at least one upper gutter portion is configured to match a profile of the at least a portion of one or more teeth on the maxilla and the retention portion of the at least one upper gutter portion is configured to extend along a crown region of the at least a portion of one or more teeth on the maxilla, wherein the retention portion of the at least one upper gutter portion is configured to be located at a side portion of the crown region of the at least a portion of one or more teeth on the maxilla; and/or the retention portion of the at least one lower gutter portion is configured to match a profile of the portion of one or more teeth on the mandible and the retention portion of the at least one lower gutter portion is configured to extend along a crown region of the at least a portion of one or more teeth on the mandible, wherein the retention portion of the at least one lower gutter portion is configured to be located at a side portion of the crown region of the at least a portion of one or more teeth on the mandible.

5. The intra-oral device according to claim 1, wherein the at least one upper gutter portion and/or the at least one lower gutter portion is configured to clip on at least one tooth that the respective gutter portion is configured to engage.

6. The intra-oral device according to claim 1, wherein the at least one upper gutter portion and/or the at least one lower gutter portion comprises at least one undercut portion configured to hold the respective gutter portion on at least one tooth located in the respective gutter portion.

7. The intra-oral device according to claim 6, wherein the at least one undercut portion is configured to extend along a side wall of one of the at least one tooth from an apex of said side wall of one of the at least one tooth in an inward direction towards the gingival part of said one of the at least one tooth, wherein the undercut portion defines an undercut.

8. The intra-oral device according to claim 1, wherein the at least one upper gutter portion and/or the at least one lower gutter portion comprises an upper sliding plane surface and/or the lower sliding plane surface, respectively, and wherein the upper sliding plane surface and/or the lower sliding plane surface is configured to extend along a major part or the entire width of at least one tooth located in the respective gutter portion in a cross sectional view of said respective gutter portion.

9. The intra-oral device according to claim 8, wherein the upper sliding plane surface and/or the lower sliding plane surface joins a side wall of the respective gutter portion in a first joining section, and wherein said side wall of the respective gutter portion is configured such that a thickness of said side wall in the area of an apex of the at least one tooth the respective gutter portion is configured to engage is less than a thickness of the side wall in the first joining section.

10. The intra-oral device according to claim 9, wherein the at least one upper gutter portion and/or the at least one lower gutter portion includes an undercut portion that intersects with an inner receiving portion of a side wall of the respective gutter portion in a second joining section, wherein the inner receiving portion angles in an outward direction.

11. The intra-oral device according claim 10, wherein the side wall of the respective gutter portion is configured such that the thickness of the side wall in the area of the apex of the at least one tooth the respective gutter portion is configured to engage is less than a thickness of a side wall of the second joining section and/or a thickness of a side wall of the inner receiving portion.

12. The intra-oral device according to claim 2, wherein the lower splint includes a lower splint connection point configured to connect with the first rod end of one of the pair of connecting rods and the upper splint includes an upper splint connection point configured to connect with the second rod end of said one of the pair of connecting rods, wherein the lower splint connection point is elevated relative to the at least one lower gutter portion.

13. The intra-oral device according to claim 12, wherein
the lower splint connection point includes a slot and the first rod end of said one of the pair of connecting rods includes a pin configured to be received in the slot of the lower splint connection point and a longitudinal axis of the slot of the lower splint connection point and a longitudinal axis of said one of the pair of connecting rods are arranged in a an obtuse angle; and
the upper splint connection point includes a slot and the second rod end of said one of the pair of connecting rods includes a pin configured to be received in the slot of the upper splint connection point and a longitudinal axis of the slot of the upper splint connection point and the longitudinal axis of said one of the pair of connecting rods are arranged in another obtuse angle, wherein an angle of the longitudinal axis of the slot of the lower splint connection point relative to the lower sliding plane surface of the at least one lower gutter portion and/or an angle of the longitudinal axis of the slot of the upper splint connection point relative to an upper sliding plane surface of the at least one upper gutter portion is adjustable.

14. The intra-oral device according to claim 13, wherein the slot of the lower splint connection point is counter sunk on the lower splint connection point and/or the slot of the upper splint connection point is counter sunk on the upper splint connection point.

15. The intra-oral device according to claim 1, wherein the upper band portion is configured to engage across the front portion of the upper central incisor teeth without engaging the internal surface of the upper central incisor teeth.

16. The intra-oral device according to claim 1, wherein the upper band portion and/or the lower band portion comprises rounded edges on a top edge and/or a bottom edge, wherein the rounded edges are drop shaped.

17. The intra-oral device according to claim 1, wherein the upper band portion and/or the lower band portion is inclined to follow an angle of the patient's incisors.

18. The intra-oral device according to claim 12, wherein the lower splint connection point is located in a wing structure with a wing base extending laterally from the at least one lower gutter portion, wherein the wing structure comprises a filled portion connecting the wing base to the lower gutter portion, the filled portion being contoured to provide support to the patient's cheek and to avoid dead space between the wing structure and said cheek.

19. The intra-oral device according to claim 18, wherein the wing base and the filled portion are configured to avoid edges, curvatures with small radii and dead space between the wing structure and the patient's cheek.

20. The intra-oral device according to claim 1, wherein the lower band portion is configured to engage the front portion of lower central incisor teeth without engaging the internal surface of the lower central incisor teeth.

21. The intra-oral device according to claim 1, wherein the lower band portion is integrally formed as a single piece with the two lower gutter portions and the lower band portion is configured to engage the front portion of lower central incisor teeth and a front portion of lower lateral incisor teeth while the two lower gutter portions are configured to engage said at least the portion of one or more teeth on the patient's mandible.

22. The intra-oral device according to claim 1, wherein a top edge and/or a bottom edge of the lower band portion comprises a tear-drop shape.

23. The intra-oral device according to claim 1, wherein a front surface of the lower band portion angles outward from a bottom to a top of the front surface of the lower band portion.

24. The intra-oral device according to claim 1, wherein the at least one upper gutter portion comprises an upper sliding plane surface and the lower sliding plane surface that is adjacent and parallel to the upper sliding plane surface, wherein a front surface of the upper band portion forms an acute angle with the upper sliding plane surface and a front surface of the lower band portion forms an acute angle with the lower sliding plane surface.

25. The intra-oral device according to claim 1, wherein the surface of the lower band portion forming the acute angle is configured to follow an angle of said lower central incisor teeth when the intra-oral device is worn by the patient.

26. The intra-oral device according to claim 1, wherein the surface of the lower band portion forming the acute angle is configured to be positioned directly in front of the lower central incisor teeth when the intra-oral device is worn by the patient.

27. The intra-oral device according to claim 1, wherein the surface of the lower band portion forming the acute angle is a front surface of the lower band portion.

* * * * *